(12) United States Patent
Nishimura et al.

(10) Patent No.: US 6,774,221 B1
(45) Date of Patent: Aug. 10, 2004

(54) PROCESS FOR ELIMINATING N-TERMINAL METHIONINE

(75) Inventors: Osamu Nishimura, Ibaraki (JP); Tsuneo Asano, Hyogo (JP); Masato Suenaga, Hyogo (JP); Hiroaki Ohmae, Nara (JP); Norio Okutani, Hyogo (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/806,871

(22) PCT Filed: Oct. 4, 1999

(86) PCT No.: PCT/JP99/05456

§ 371 (c)(1),
(2), (4) Date: May 7, 2001

(87) PCT Pub. No.: WO00/20439

PCT Pub. Date: Apr. 13, 2000

(30) Foreign Application Priority Data

Oct. 5, 1998 (JP) .......................................... 10/282476

(51) Int. Cl.$^7$ ............................ C08H 1/00; C07K 1/107
(52) U.S. Cl. ....................... 530/402; 530/333; 530/345; 530/399; 435/69.1
(58) Field of Search ................................. 530/333, 345, 530/399, 402; 435/69.1

(56) References Cited

U.S. PATENT DOCUMENTS 6,309,859 B1 * 10/2001 Nishimura et al. ........ 435/69.1

FOREIGN PATENT DOCUMENTS

| EP | 193515 | 9/1986 |
| EP | 812856 | 12/1997 |
| WO | 86/01229 | * 2/1986 |

* cited by examiner

Primary Examiner—Christopher S. F. Low
Assistant Examiner—David Lukton
(74) Attorney, Agent, or Firm—Wenderoth, Lind & Ponack L.L.P.

(57) ABSTRACT

A method for removing from a peptide the diketone of the methionine residue, and a method for manufacturing a peptide or salt thereof which does not possess an N-terminal methionine residue, characterized by having a peptide or salt thereof which possesses a diketone of the optionally oxidized N-terminal methionine residue react with 3,4-diaminobenzoic acid or a salt thereof in the presence of acetic acid and sodium formate, formic acid and sodium formate, or formic acid and sodium acetate.

12 Claims, 6 Drawing Sheets

Fig. 4

1  5'CTAGAAAGGAGATATCATATGCTGGTTCAACCGCGTGGTTCT

2  5'CGTAATGGTCCGGGTCCATGGCAAGGTGGTCGTCGTAAATTTCGTC

3  5'GTCAACGTCCGCGTCTGTCTCATAAAGGTCCGATGCCCGTTTTGCC

4  5'GACCATTACGAGAACCACGCGGTTGAACCAGCATATGATATCTCCTTT

5  5'GGACGTTGACGACGAAATTACGACGACCACCTTGCCATGGACCCG

6  5'TCGGGGCAAAACGGCATCGGACCTTTATGAGACAGACGC

SEQUENCE LISTING

<160> NUMBER OF SEQ ID NOS: 10

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: DNA PRIMER

<400> SEQUENCE: 1
ctagaaagga gatatcatat gctggttcaa ccgcgtggtt ct                           42

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: DNA PRIMER

<400> SEQUENCE: 2
cgtaatggtc cgggtccatg gcaaggtggt cgtcgtaaat ttcgtc                       46

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: DNA PRIMER

<400> SEQUENCE: 3
gtcaacgtcc gcgtctgtct cataaaggtc cgatgccgtt ttgcc                        45

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: DNA PRIMER

<400> SEQUENCE: 4
gaccattacg agaaccacgc ggttgaacaa gcatatgata tctccttt                     48

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: DNA PRIMER

<400> SEQUENCE: 5
ggacgttgac gacgaaattt acgacgacca ccttgccatg gacccg                       46

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: DNA PRIMER

<400> SEQUENCE: 6
tcggggcaaa acggcatcgg acctttatga gacagacgc                               39

<210> SEQ ID NO 7
<211> LENGTH: 10

-continued

```
<212> TYPE: DNA
<213> ORGANISM: Artificial Sequence
<220> FEATURE:
<223> OTHER INFORMATION: Description of Artificial Sequence: DNA PRIMER

<400> SEQUENCE: 7
tatggatggg                                                              10

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: DNA PRIMER

<400> SEQUENCE: 8
aattcccatc ca                                                           12

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: DNA PRIMER

<400> SEQUENCE: 9
atacatatgg atgggaattc ca                                                22

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: DNA PRIMER

<400> SEQUENCE: 10
ccggatccta gtaaaacaag tcaactct                                          28
```

PROCESS FOR ELIMINATING N-TERMINAL METHIONINE

This application is a 371 of PCT/JP99/05456 filed Oct. 4, 1999.

FIELD OF THE INVENTION

This invention relates to a method for the efficient removal, from peptides (including proteins) or salts thereof which possess an optionally oxidized N-terminal methionine residue or diketone of said methionine residue, of the N-terminal methionine residue or the diketone of said methionine residue, in the presence of acetic acid and sodium formate, formic acid and sodium formate, or formic acid and sodium acetate; and to a method for manufacturing peptides or salts thereof which do not possess an optionally oxidized N-terminal methionine residue or diketone of said methionine residue.

BACKGROUND ART

When protein is biosynthesized within a cell, its N-terminal is known to start with methionine, which corresponds to the initiation codon AUG of the mRNA. However, as this methionine is removed by subsequent processing, it is usually no longer present in the completed mature protein molecule.

With advancements in recombinant DNA techniques, it has become possible to produce useful proteins using microorganisms and/or animal cells, for example *Escherichia coli*. There have been instances wherein protein produced via this type of method was found to retain a residue comprised of the aforementioned methionine. For example, the retention rate of methionine was as high as approximately 100% in human growth hormone expressed in *E. coli* [Nature, 293, 408 (1981)], and 50% in interferon-α [J. Interferon Res., 1, 381 (1981)], while in nonglycosylated human interleukin-2 the presence of a molecular species with methionine retention on the amino-terminal (N-terminal methionine residue) (Met-rIL-2) has been noted in addition to the molecular species rIL-2 which, like naturally-occurring human interleukin-2, is initiated with alanine.

In regards to method for removing N-terminal amino acid chemically, Dixon reported in 1964 that DL-alanylglycine reacts with glyoxylic acid, pyridine, or cupric acetate in a transamination that results in the production of pyruvoylglycine [Biochem. J, 92, 661 (1964)]. He further reported that thiosemicarbazide reacts with compounds to result in amide bond cleavage, producing glycine [Biochem. J. 90, 2C (1964)]. He subsequently applied this reaction to Pseudomonas cytochrome c-551, reporting the removal of N-terminal glutamic acid [Biochem. J, 94, 463 (1965)].

It is reasonable to speculate that the proteins of molecular species that do or do not possess N-terminal methionine might differ from each other in terms of their superstructure, biological activity, and/or stability, and further, that the addition of methionine to the N-terminal could bring about an increase in antigenicity. It is therefore reasonable to surmise, from the perspective of industrial utility, that it is of significance to establish a method for removing the N-terminal methionine that corresponds to the initiation codon.

With the objective of resolving this problem, a method has been proposed wherein methionine is removed via digestion by cyanogen bromide (BrCN) [Science, 198, 1056 (1977)]. However, in addition to presupposing the absence of methionine residue within the desired mature protein, this method, which subjects the protein to harsh chemical reactions, is by no means conducive to satisfactory results.

Aside from the method described in Unexamined Kokai Application Heisei 10-72489 (EP-A-812856), chemical methods which remove the N-terminal methionine residue from peptides or proteins which possess an N-terminal methionine residue in a selective and efficient manner regardless of the type of peptide or protein, are not known. This is most likely attributable to the difficulty of identifying a chemical reaction that is capable of removing N-terminal methionine under gentle conditions without altering the final product, i.e. the peptide or protein. In particular, as the removal of excess N-terminal methionine from genetically engineered proteins of relatively large molecular weight, particularly those intended for use as pharmaceutical agents, requires the activity of the protein not to deteriorate upon methionine removal, the reaction usually needs to proceed, without heating, in alkalescent to acescent solutions. As this is extremely restrictive by chemical reaction conditions, the current situation has been such that a favorable set of reaction conditions could not be identified.

DISCLOSURE OF THE INVENTION

The inventors, upon diligent study with the objective of providing, via the exclusive cleavage of the N-terminal methionine residue in peptides (including proteins) manufactured via genetic engineering, a method for the manufacture of peptides with amino acid sequences that mimic naturally occurring sequences, have discovered that it is possible to remove, from peptides which possess a diketone of themethionine residue, the diketone of said methionine residue by having a peptide which possesses an optionally oxidized N-terminal methionine residue, as represented in Formula (I) of Scheme 1 below, undergo transamination with, for example, glyoxylic acid, which is an α-diketone, or cupric sulfate, which is capable of providing transition metal. ions, or pyridine, which is a base (for example, an amine), to yield a peptide which possesses a diketone of the said methionine residue, which, when allowed to react with 3,4 diaminobenzoic acid, which is a base (for example, a diamine), in the presence of acetic acid and sodium formate, formic acid and sodium formate, or formic acid and sodium acetate, followed by hydrolysis, it is possible to remove the diketone of the methionine residue from the peptide which possesses the diketone of the methionine residue in an unexpectedly efficient manner. Hence the inventors, having identified a method of removing, at an unexpectedly high yields, the optionally oxidized N-terminal methionine residue from peptides which possess methionine residue, to obtain, without bringing about a deterioration in activity, peptides which do not possess optionally oxidized N-terminal methionine residue, further pursued their studies to achieve the completion of the present invention.

(Scheme 1)

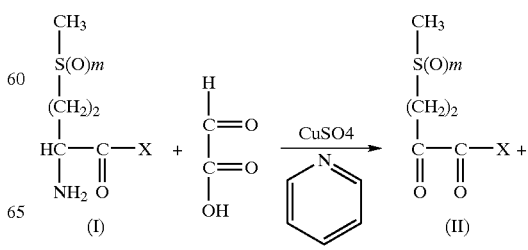

-continued

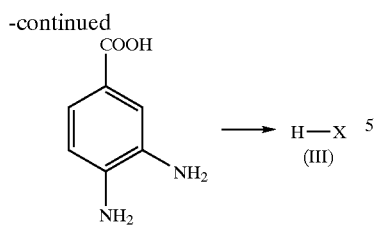

[In formula (I), m represents the integer 0 or 2, while X can be any peptide chain possessing either an amino acid residue or at least 2 amino acids, although from a practical standpoint, an example would be a peptide chain that corresponds to the X of a protein manufactured via genetic engineering. In the specification of the present patent, the term "protein" or "peptide" may refer to a peptide comprised of multiple amino acids or, in the case of a protein, may refer to either a nonglycosylated or glycosylated peptide or protein.]

In the specification of the present patent, within Scheme 1 above,

The compound represented by general formula (I) can be referred to as "a peptide which possesses optionally oxidized N-terminal methionine residue" or "a peptide which possesses methionine residue";

The partial-structure within general formula (I) that is represented as

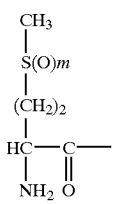

[m within the formula having the same meaning as mentioned above] can be referred to as "optionally oxidized methionine residue," "methionine residue," or "methionine";

The compound represented by general formula (II) can be referred to as "a peptide which possesses the diketone of the optionally oxidized N-terminal methionine residue" or "a peptide which possesses the diketone of the methionine residue";

The partial structure within general formula (II) that is represented as

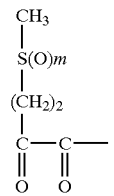

[m within the formula having the same meaning as mentioned above] can be referred to as "diketone of the optionally oxidized methionine residue" or "diketone of the methionine residue"; and The compound represented by general formula (III) can be referred to as "a peptide which does not possess optionally oxidized N-terminal methionine residue" or "a peptide which does not possess the diketone of the optionally oxidized N-terminal methionine residue."

Hence, the present invention relates to (1) a method for removing the diketone of N-terminal methionine residue characterized by having a peptide or the salt thereof that possesses the diketone of an optionally oxidized N-terminal methionine residue, react with 3,4-diaminobenzoic acid or the salt thereof in the presence of acetic acid and sodium formate, or formic acid and sodium formate, or formic acid and sodium acetate, (2) the method described in (1) above wherein the peptide or the salt thereof which possesses the diketone of the optionally oxidized N-terminal methionine residue is a peptides or the salt thereof that is obtained by having a peptide or the salt thereof that possesses optionally oxidized N-terminal methionine residue react with an α-diketone, (3) the method described in (2) above wherein the peptide that possesses optionally oxidized N-terminal methionine is a peptide that has been manufactured via genetic engineering, (4) the method described in (1) above wherein the peptide is a (i) growth hormone, (ii) β-cellulin, (iii) interleukin-2, (iv) neutrophin-3, or (v) apelin, (5) the method described in (1) above wherein the peptide is a growth hormone, (6) the method described in (1) above which is characterized by the acetic acid and sodium formate, or formic acid and sodium formate, or formic acid and sodium acetate, being used as a buffering solution of approximately 0.1 to 8 mol/L with a pH of approximately 2 to 9, (7) a method for removing the diketone of the N-terminal methionine residue characterized by having a peptide or the salt thereof which possesses the diketone of the optionally oxidized N-terminal methionine residue react with 3,4-diaminobenzoic acid or the salt thereof in the presence of acetic acid and sodium formate, (8) a method of manufacturing a peptide or the salt thereof which does not possess the optionally oxidized N-terminal methionine residue characterized by having a peptide or the salt thereof which possesses the diketone of the optionally oxidized N-terminal methionine residue react with 3,4-diaminobenzoic acid or the salt thereof in the presence of acetic acid or sodium formate, or formic acid and sodium formate, or formic acid and sodium acetate, (9) a method of manufacture described in (8) above wherein the peptide or the salt thereof that possesses the diketone of the optionally oxidized N-terminal methionine residue is a peptide or the salt thereof that is obtained by having a peptide or the salt thereof which possesses optionally oxidized N-terminal methionine residue react with an α-diketone,

(10) a method of manufacture described in (8) above characterized by the acetic acid and sodium formate, or formic acid and sodium formate, or formic acid and sodium acetate, being used as a buffering solution of approximately 0.1 to 8 mol/L with a pH of approximately 2 to 9,

(11) a method of manufacturing a peptide or the salt thereof that does not possess N-terminal methionine residue characterized by having a peptide or the salt thereof which possesses the diketone of the optionally oxidized N-terminal methionine residue react with 3,4-diaminobenzoic acid or the salt thereof in the presence of acetic acid and sodium formate,

(12) a method of manufacturing human growth hormone or the salt thereof which does not possess N-terminal methionine residue characterized by having the human growth hormone or the salt thereof that is manufactured via genetic engineering which possesses optionally oxidized N-terminal methionine residue react with glyoxylic acid or the salt thereof in the presence of cupric sulfate and pyridine, and subsequently with 3,4-diaminobenzoic acid or the salt thereof in the presence of acetic acid and sodium formate, or formic acid and sodium formate, or formic acid and sodium acetate,

(13) the use of (i) acetic acid and sodium formate, or formic acid and sodium formate, or formic acid and sodium acetate, and (ii) 3,4-diaminobenzoic acid or the salt thereof, for the purpose of removing the N-terminal methionine residue from a peptide or the salt thereof which possesses optionally oxidized N-terminal methionine residue,

(14) the use of (i) acetic acid and sodium formate, or formic acid and sodium formate, or formic acid and sodium acetate, and (ii) 3,4-diaminobenzoic acid or the salt thereof, for the purpose of removing the diketone of the methionine residue from a peptide or the salt thereof which possesses the diketone of the optionally oxidized N-terminal methionine residue,

(15) the use of (i) acetic acid and sodium formate, or formic acid and sodium formate, or formic acid and sodium acetate, and (ii) 3,4-diaminobenzoic acid or the salt thereof, for the purpose of manufacturing a peptide or the salt thereof which does not possess optionally oxidized N-terminal methionine residue from a peptide or the salt thereof which possesses optionally oxidized N-terminal methionine residue,

(16) the use of (i) acetic acid and sodium formate, or formic acid and sodium formate, or formic acid and sodium acetate, and (ii) 3,4-diaminobenzoic acid or the salt thereof, for the purpose of manufacturing a peptide or the salt thereof which does not possess the diketone of the optionally oxidized N-terminal methionine residue from a peptide or the salt thereof which possesses the diketone of the optionally oxidized N-terminal methionine residue.

BRIEF DESCRIPTION OF THE DRAWINGS

FIG. 4 is an illustration of the DNA fragment used in Example 26.

BEST MODE OF EMBODIMENT OF THE INVENTION

Figure 1:
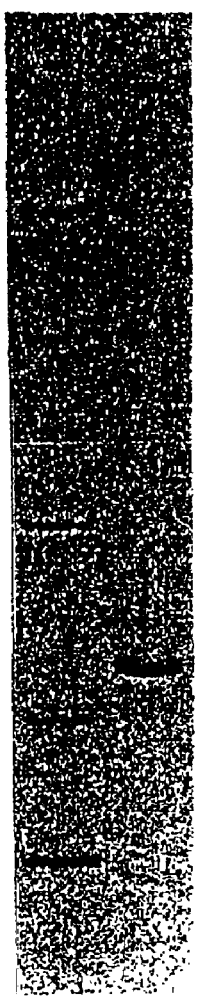
FIG. 1 is an illustration of the results of electrophoresis obtained in Example 4a). Lane 1 represents the molecular weight marker, while Lane 2 represents the purified hGH.

In the specification of the present patent, the optionally oxidized methionine residue indicates the methionine residue or its sulfoxide, while the sulfoxide of the methionine residue can include methionine sulfoxide or methionine sulfone.

While a peptide which possesses optionally oxidized N-terminal methionine residue can indicate a peptide which is represented by the formula $CH_3$—$S(O)_m$—$(CH_2)_2$—CO—X [where m indicates the integer 0 or 2, and X indicates the amino acid residue or the peptide chain], such peptide can also be in the form of a salt, of which any kind is acceptable insofar as such salt does not inhibit the reaction of the present invention, but which preferably is a pharmaceutically acceptable salt including a salt with an inorganic acid such as hydrochloric acid, hydrobromic acid, nitric acid, sulfuric acid, or phosphoric acid, a salt with an organic acid such as acetic acid, pthalic acid, fumaric acid, tartaric acid, maleic acid, citric acid, succinic acid, methanesulfonic acid, or para-toluenesulfonic acid, an alkaline metal salt such as a sodium salt or a potassium salt, an alkaline earth metal salt such as calcium salt, or an ammonium salt.

A peptide which possesses optionally oxidized N-terminal methionine residue is preferably a peptide manufactured by genetic engineering which possesses optionally oxidized N-terminal methionine residue.

In the formula above, 0 is preferable as the m, while a peptide chain with at least two amino acids is preferable as X.

The peptide in the present invention can either be a "peptide," with fewer than 50 amino acids, or a. "protein," with at least 50 amino acids.

In this manner, while the term "peptide" in the specification of the present patent includes not only a molecule with fewer than 50 amino acids but also a molecule with at least 50 amino acids, it is preferable to use a molecule with at least 50 amino acids ("a protein").

A preferable peptide is a peptide comprised of 2 to 1,000 amino acids, of which a particularly preferable peptide is one comprised of 15 to 500 amino acids, of which a specific example is a protein such as a growth hormone (GH) [for example, human growth hormone (hGH) (e.g. 20K-hGH and 22K-hGH)], β-cellulin (BTC), parathyroid hormone (PTH), insulin, nerve growth factor, brain derived neurotrophic factor, ciliary neurotrophic factor, glial cell line derived neurotrophic factor, neurotrophin-3, -4, or -6, central nervous system growth factor, glial growth factor, lung derived neurotrophic factor, epidermal growth factor, fibroblast growth factor, platelet derived growth factor, transforming growth factor α or β, vascular endothelial growth factor, tissue plasminogen activator, urokinase, protein C, thrombomodulin, bone growth factor, calcitonin, insulin-like growth factor, interferon-α, β, or -γ, interleukin-1 (α, β) to interleukin-12, granulocyte colony-stimulating factor, granulocyte-macrophage colony-stimulating factor, granulocyte-macrophage stimulating factor, thrombopoietin, erythropoietin, PACAP, atrial natriuretic peptide, endoserine, megakaryocyte growth and development factor, hematopoietic stem cell growth factor, hepatocyte growth factor, motilin, immunotoxin, tumor necrosis factor, hirudin, corticotropin, angiotensin, angiotensin 2 and its peptide antagonist, angiotensin 3, bradykinins, bradykinin-potentiating factor, α-, β-, or γ-endorphin, enkephalin, neutrophil chemotactic factor, gastrin, glucagon, growth hormone releasing factor, kyotorphine, kallidin, gonadotropin-releasing hormone, mast cell degranulating peptide, melanocyte stimulating hormone, neurotensin, trypsin inhibitor, oxytocin, proinsulin C-peptide, secretin, somatostatin, thyrotropin releasing hormone, ubiquitin, urogastrone, vasopressins, kinins, tuftsin, somatomedin, corticotropin releasing factor, insulin-like growth factor, calcitonin gene-related peptide, PTHrP, VIP, DHI, insulinotropin, GRP, CCK-PZ, galanin, antrum peptide, PPY, pancreatic polypeptide, PSP, pancreastatin, hCG, hCS, relaxin, serum thymic factor, thymopoetin, thymosin, Factor XIII, Factor VIII, prourokinase, SOD, Factor VIIa, antithrombin, or apelin, or the mutein thereof (in which at least one amino acid is replaced, deleted, or added in a wild type protein, showing a biological or immunological activity equal to or greater than that of the wild type protein), or a known or new peptide manufactured via a method such as chemical synthesis, of which a particularly preferable peptide for use is a peptide (which can also be a protein) manufactured via genetic engineering, in particular a growth hormone manufactured via genetic engineering [for example, human growth hormone (hGH) (e.g. 20K-hGH and 22K-hGH)], neurotrophin-3, β-cellulin, parathyroid hormone, interleukin-2, apelin, or the mutein thereof, in particular a growth hormone [for example, human growth hormone (hGH) (e.g. 20K-hGH and 22K-hGH)]. The aforementioned apelin can be, for example, as described in Biochem. Biophys. Res. Commun., 251, 471–476 (1998), human apelin-36, human apelin-13, or a peptide in which the N-terminal amino acid (Gln) of apelin-13 has been converted to pyroglutamic acid; any type of peptide is acceptable insofar as such peptide has ligand activity toward APJ (O'Dowd, B. F., et al, Gene, 436, 355–359 (1993)), a specific example of which is, as described in Patent Application Heisei 10-271654, "a polypeptide which has the capability to bind with a receptor protein which has an identical, or practically identical, amino acid sequence to the amino acid sequence represented by sequence number: 3."

While the aforementioned peptide (which can also be a wild type protein) mentioned above can be derived from any animal species, a human derived peptide (which can also be a protein) is preferable for practical use.

The aforementioned peptide can be refolded (activated, regenerated) prior to or following being subjected to the process of removing the optionally oxidized N-terminal methionine (Met) residue or the diketone of said methionine residue.

In the specification of the present patent, a peptide or the salt thereof which possesses the diketone of the optionally oxidized N-terminal methionine residue indicates a compound or the salt thereof which is represented by the formula $CH_3$—$S(O)_m$—$(CH_2)_2$—CO—CO—X [where m indicates the integer 0 or 2, and X indicates the amino acid residue or the peptide chain]. The peptide or the salt thereof which possesses the diketone of the optionally oxidized N-terminal methionine residue can be obtained via a variety of reactions, such as a chemical reaction or an enzyme reactions. For example, a method of chemical reaction might be one in which a peptide or the salt thereof which possesses the diketone of the optionally oxidized N-terminal methionine residue is obtained via transamination, in which a peptide or the salt thereof which possesses optionally oxidized N-terminal methionine residue is made to react with an α-diketone (Unexamined Kokai Application Heisei 10-72489 (EP-A-812856)).

In the specification of the present patent, the α-diketone can be of any kind insofar as such α-diketone allows the transamination of the above mentioned peptide or the salt thereof to proceed, an examples of which is a compound represented by the formula $R^1$—CO—CO—$R^2$ [where $R^1$ indicates a low alkyl or phenyl group optionally substituted with hydrogen or a carboxyl group (preferably hydrogen or methyl, more preferably hydrogen), and $R^2$ indicates an amino group optionally substituted with a hydroxyl group, low alkoxy group, or low alkyl (preferably a hydroxyl group)], or the salt thereof.

In the above formula, an example of the low alkyl group indicated by $R^1$ is an alkyl group with 1 to 6 carbons, such as methyl, ethyl, propyl, i-propyl, butyl, i-butyl, sec-butyl, or t-butyl, while an example of the low alkoxy group indicated by $R^2$ is an alkoxy group with 1 to 6 carbons, such as methoxy, ethoxy, propoxy, i-propoxy, butoxy, i-butoxy, sec-butoxy, or t-butoxy. An example of the amino group optionally substituted with low alkyl indicated by $R^2$ is an amino group that can have one or two low alkyl groups indicated by aforementioned $R^1$. An example of a salt is a salt that is similar to a salt of the aforementioned peptide which possesses optionally oxidized N-terminal methionine residue.

Some specific examples of an α-diketone would be glyoxylic acid, pyruvic acid, oxalacetic acid, phenylglyoxylic acid, and 2-oxoglutaric acid, of which glyoxylic acid is particularly preferable for use.

The α-diketone can be in the form of a salt, of which an example is an alkaline metal salt such as a sodium salt or a potassium salt, or an inorganic salt such as a hydrochloride.

The transamination of a peptide or the salt thereof which possesses an optionally oxidized N-terminal methionine residue with an α-diketone is usually preferably conducted with approximately 1 to 10,000 moles (preferably 2,000 to 4,000 moles) of α-diketone for 1 mol of peptide or the salt thereof, at approximately 0 to 70° C. (preferably approximately 20 to 40° C.) for approximately 10 minutes to 5 hours (preferably approximately 20 minutes to 2 hours). Insofar as it does not inhibit the above-mentioned transamination, any buffer solution can be used (e.g. phosphate buffer solution, acetate buffer solution, or citrate buffer solution), although acetate buffer solution is particularly preferably for use. The pH for the reaction is best adjusted to approximately 2 to 9, in particular approximately 4 to 7, above all approximately 5 to 6, for the reaction to proceed.

To facilitate the said transamination, it is preferable to have the α-diketone react in the presence of a transition metal ion, of which the use of approximately 0.001 to 0.1 moles (preferably 0.01 to 0.05 moles) of transition metal ion to 1 mole of α-diketone is usually preferable. Examples of transition metal ions that can be used include copper ($Cu^+$, $Cu^{2+}$), cobalt ($Co^{2+}$, $Co^{3+}$), nickel ($Ni^{2+}$, $Ni^{3+}$), iron ($Fe^{2+}$, $Fe^{3+}$) zinc ($Zn^{2+}$), aluminum ($Al^{3+}$), manganese (e.g. $Mn^{2+}$), gallium ($Ga^{3+}$), indium ($In^{3+}$), magnesium ($Mg^{2+}$), and calcium ($Ca^{2+}$), out of which such ions as copper or cobalt, in particular copper ($Cu^{2+}$), is particularly preferable for use. The transition metal ion can be added to the reaction solvent, usually in the form of a salt of an inorganic acid such as sulfuric acid, nitric acid, hydrochloric acid, or perchloric acid, or of an organic acid such as acetic acid, oxalic acid, citric acid, or carbonic acid, of which cupric sulfate or cupric acetate, particularly cupric sulfate, is preferable for use Additionally, it is preferable to have the α-diketone react in the presence of a base, wherein 0.1 to 20 moles (preferably 0.5 to 10 moles) of base for 1 mole of α-diketone is usually preferable for use. Some examples of a base include an alkylamine such as triethylamine, tributylamine, or an aromatic amine such as N,N-dimethylaniline, pyridine, lutidine, collidine, 4-(dimethylamino)pyridine, or imidazole, of which pyridine is particularly preferable for use.

Additionally, for the purposes of preventing the precipitation during transamination of the peptide or the salt thereof which possesses an optionally oxidized N-terminal methionine residue, or the peptide or the salt thereof which possesses the diketone of the methionine residue obtained via transamination of the peptide or the salt thereof which possesses an optionally oxidized N-terminal methionine residue, it is preferable to add urea to the transamination buffer solution in accordance with the type of said peptide, peptide which possesses the diketone of the methionine residue, or the salt thereof. For example, when using hGH, it is preferable to add urea to the buffer solution so that the concentration is approximately 1 to 8 M, more preferably approximately 3 to 6 M.

Further, in the aforementioned transamination, it is preferable to have the α-diketone react in the presence of a transition metal ion and a base, wherein for practical purposes, the transamination is made to proceed with the addition of a mixed solution containing the three components of transition metal ion; base, and α-diketone (for example, cupric sulfate, pyridine, and glyoxylic acid) to the aqueous solution containing the peptide or the salt thereof which possesses optionally oxidized N-terminal methionine residue.

While the compound or the salt thereof that is obtained by said transamination and is represented by the formula $CH_3$—$S(O)_m$—$(CH_2)_2$—CO—CO—X [where m indicates the integer 0 or 2, and X indicates the amino acid residue or peptide chain] can be isolated from the reaction solution and purified via known procedures for peptide or protein purification, for example, extraction, salting out, distribution, recrystallization, or chromatography, said compound or the salt thereof can also be subjected, as is, to the following hydrolysis reaction.

The peptide or the salt thereof obtained via the transamination which possesses the diketone of the methionine can usually be converted to an amino acid, peptide, or the salt thereof which does not possess optionally oxidized N-terminal methionine residue or diketone of said methionine residue.

While the base used in the hydrolysis reaction can be, for example, an alkylamine such as cysteamine, triethylamine, or tributylamine, or a salt thereof, an aromatic amine such as N,N-dimethylaniline, pyridine, lutidine, collidine, 4-(dimethylamino)pyridine, or imidazole, or a salt thereof, a diamine (preferably an aromatic diamine, in particular 3,4-diaminobenzoic acid or an n-alkyl substitution thereof (for example, n-methyl-1,2-phenylenediamine, n-ethyl-1,2-phenylenediamine, or n-isopropyl-1,2-phenylenediamine) such as o-phenylenediamine, tolylene-3,4-diamine, 3,4-diaminobenzoic acid or an n-alkyl substitution thereof (for example, n-methyl-1,2-phenylenediamine, n-ethyl-1,2-phenylenediamine, or n-isopropyl-1,2-phenylenediamine), 2,3-diaminophenol, or 4-chloro-o-phenylenediamine, or a salt thereof, a thiosemicarbazide such as thiosemicarbazide, acetone thiosemicarbazide, or phenyl thiosemicarbazide, a selenosemicarbazide such as selenosemicarbazide or acetone selenosemicarbazide or a salt thereof, an amine is preferable, in particular a diamine or thiosemicarbazide or a salt thereof, and especially 3,4-diaminobenzoic acid or a salt thereof.

An example of a base that can be used in the hydrolysis reaction can be a base which is similar to a salt of the peptide which possesses optionally oxidized N-terminal methionine residue mentioned above.

The amount of base is usually approximately 1 to 10,000 moles for 1 mole of the peptide which possesses the diketone of the methionine residue, or the salt thereof, preferably approximately 200 to 3,000 moles, and more preferably, approximately 500 to 3,000 moles. The hydrolysis reaction is usually made to proceed at approximately 0 to 70° C.

(preferably approximately 20 to 40° C.) for approximately 1 hour to 7 days (preferably approximately 10 hours to 5 days). It is preferable to use a buffer solution as the solvent in the reaction, an example of such a buffer solution being a formic acid buffer (for example, acetic acid-sodium formate, formic acid-sodium formate, or formic acid-sodium acetate), while any buffer solution can be used insofar as such buffer solution does not inhibit the aforementioned hydrolysis reaction, an acetic acid-sodium formate, formic acid-sodium formate, or formic acid-sodium acetate buffer solution is particularly preferable. The pH for the reaction is best adjusted to approximately 2 to 9, in particular approximately 3 mn to 7, above all approximately 4 to 6, for the reaction to proceed. The amount of buffer solution to use is preferably approximately 0.1 to 8 mol/L, and more preferably approximately 0.5 to 6 mol/L.

In order to prevent the precipitation of the amino acid, peptide, or salt thereof which does not possess optionally oxidized N-terminal methionine obtained via hydrolysis of a peptide or salt thereof which possesses a diketone of optionally oxidized N-terminal methionine, it is preferable to add urea to the buffer solution for hydrolysis in accordance with the type of said peptide which possesses a diketone of optionally oxidized N-terminal methionine and the type of said amino acid, peptide, or salt thereof which does not possess methionine residue. For example, when using hGH, it is preferable to add urea to the buffer solution so that the concentration is approximately 1 to 6 M, more preferably approximately 2 to 5 M.

While the amino acid, peptide, or salt thereof obtained in this way can be isolated from the reaction solution and purified via known methods of purification, for example extraction, salting out, distribution, recrystallization, or chromatography, a preferable example is purification via ion exchange chromatography using SP-Sepharose (Pharmacia Biotech) or DEAE-5PW (Tosoh Corporation).

As the peptide manufactured in the present invention is obtained in a form that does not possess methionine on its N-terminal, and that furthermore has an amino acid sequence identical to that of the biologically active target peptide (for example, a biologically active native polypeptide), such peptide possesses similar activity to that of the target peptide (for example, a native polypeptide), has a low toxicity, and can be used safely as a pharmaceutical or diagnostic agent.

The present invention makes possible the specific removal of the methionine residue or the diketone of said methionine residue from a peptide which possesses an optionally oxidized N-terminal methionine residue or a diketone of said methionine residue.

Where abbreviations have been used to indicate amino acids etc. in the patent specification or drawing of the present invention, such abbreviations are in accordance with the IUPAC-IUB Commission on Biochemical Nomenclature or in common use in the relevant field, as shown in the examples below. When an amino acid shows optical isomerism, the L-form is indicated unless explicitly stated otherwise.

SDS: sodium dodecyl sulfate
Gly: glycine
Ala: alanine
Val: valine
Leu: leucine
Ile: isoleucine
Ser: serine Thr: threonine
Cys: cysteine
Met: methionine
Glu: glutamic acid
Gln: glutamine
Asp: aspartic acid
Asn: asparagine
Lys: lysine
Arg: arginine
His: histidine
Phe: phenylalanine
Tyr: tyrosine
Trp: tryptophan
Pro: proline
Asx: Asp+Asn
Glx: Glu+Gln While the present invention is more specifically described by the references and examples below, the present invention is not limited by these references and examples.

Reference 1 (Construction of Human Growth Hormone (hGH) Expression Vector Using T7 Promoter)

The structural gene for hGH was recovered from a human pituitary cDNA library (Quick-Clone, CLONTECH Laboratories, Inc.) via PCR amplification using a primer with an Nde I cleavage site immediately upstream of the initiation codon of the structural gene, and a primer with a Bam HI cleavage site immediately downstream of the termination codon of the structural gene. The hGH enzyme gene thus obtained with restriction enzyme recognition sites added at both ends was ligated into the T-cloning site of pT7 Blue (DNA Ligation Kit Ver. 2, Takara Shuzo Co., Ltd.) to create pT7HGH-Na. This was introduced into E. coli JM109, whereupon transformants were selected by ampicillin resistance and β-galactosidase activity.

Meanwhile, the expression vector was constructed in the following manner. pBR322 was cut with Nde I, whereupon the ends were blunted with T4 DNA polymerase (DNA Blunting Kit, Takara Shuzo Co., Ltd.), then religated, to yield pBRdesNde with the Nde I recognition site deleted. pET3c was cut with Bgl II-Eco RV, whereupon fragments of approximately 0.26 kbp were recovered, then the ends blunted with T4 DNA polymerase, and subsequently ligated into Sca I fragments of pBRdesNde, to yield pBR/T7 desNde. Additionally, by site-directed mutagenesis (Quick Change, Stratagene) pBR322desBam, lacking the Bam HI recognition site of pBR322 was prepared. The Sph I-Eco RV fragment of pBR322desBam was ligated to the Sph I-Eco RV fragment of pBR/T7 desNde to yield the tetracycline resistant expression vector pTC. Vectors in which the tetracycline resistant gene and the T7 promoter were in the opposite direction were designated pTC1, while vectors in which said gene and promoter were in the same direction were designated pTC2.

pT7HGH-Na was cut with Nde I and Bam HI to harvest the hGH structural gene, which was then ligated into the Nde I-Bam HI fragment of pTC1, then subsequently introduced into E. coli JM109, whereupon transformants were selected by ampicillin resistance, from which strain plasmids were recovered, and designated expression plasmid pTCHGH-Na.

E. coli MM294 was lysogenized by a recombinant lambda-phage containing the T7 RNA polymerase gene (Studier, supra). Subsequently, the hGH expression vector pTCHGH-Na was introduced into this E. coli MM294 (DE3), to yield E. coli MM294(DE3)/pTCHGH-Na. The base sequence of hGH was confirmed by DNA sequencer ABI Prism 377A at the time pT7HGH-Na was created.

Reference 2 (Expression of hGH which Possesses Methionine Residue (Met-hGH) in E. coli)

The transformed cells obtained in Reference 1 were subjected to 16 hours of shake culture at 30° C., within a 2-liter flask containing 1 liter of LB medium (1% peptone, 0.5% yeast extract, 0.5% sodium chloride) containing 5 mg/L tetracycline. The culture solution obtained was transplanted to a 50 liter fermenter with 20 liters of LB medium containing 0.02% Newpol LB-625 (antifoaming agent, Sanyo Chemical Industries Ltd.) and 5 mg/L tetracycline, to undergo 6 hours of aeration/agitation at 37° C. This culture solution was transplanted to a 500 liter fermenter containing 360 liters of fermentation medium (1.68% dibasic sodium phosphate , 0.3% monobasic potassium phosphate, 0.1% ammonium chloride, 0.05% sodium chloride, 0.05% magnesium sulfate, 0.05% Newpol LB-625, 0.0005% thiamine hydrochloride, 1.5% glucose, 3.0% Hy-Case Amino, 1.0% yeast extract), to start aeration/agitation at 37° C. When the turbidity of the culture reached approximately 1,200 Klett units, 17.85 mg/L of isopropyl-β-D-thiogalactopyranoside (IPTQ) was added, with a further 24 liters of 30% glucose added while culturing was continued, whereupon 5 hours later the culture was subjected to centrifugation to obtain approximately 12.3 kg of wet cells, which were then frozen for storage at −80° C.

The aforementioned transformed E. coli (MM294(DE3). pTCHGH-Na) was deposited with the National Institute of Bioscience and Human-Technology of the Agency of Industrial Science and Technology of the Ministry of International Trade and Industry on Dec. 10, 1997, under accession number FERM P-16546, which was then. transferred to an international depository on Sep. 24, 1999, under accession number FERM BP-6888. The aforementioned transformed E. coli (MM294(DE3), PTCHGH-Na) was deposited with the Institution for Fermentation, Osaka (IFO) on Oct. 16, 1997, under accession number IFO 16124.

EXAMPLE 1

Activation of Met-hGH

To 2 kg of the cells obtained in Reference 2, 6 liters of 50 mM Tris/HCl and 8M guanidine hydrochloride solution (pH 8.0) was added to dissolve the cells, which were then subjected to sonication using an ultrasonic cell disrupter (Sonifier 450, Branson Ultrasonics corporation), then subsequently subjected to centrifugation (10,000 rpm for 120 minutes). To 6 liters of the supernatant obtained, 18 liters of 50 mM Tris/HCl, 0.28 mM GSSG, 1.4 mM GSH, and 0.7 M arginine (pH 8.0) was added, the pH adjusted to 8.0, and activation conducted for 4 days at 4° C.

EXAMPLE 2

Purification of Met-hGH

The regenerant which underwent activation in Example 1 was desalted and concentrated in a Pellicon cassette system (PTGC membrane, Millipore Corporation) with the addition of 20 mM Tris/HCl and 2.5 M urea (pH 8.0), until the electric conductivity was no greater than 10 mS, whereupon 50 mM phosphate buffer solution (pH 6.0) was added to 5 liters of the concentrate obtained to dilute it to 50 liters, which was then allowed to stand overnight at 4° C. Subsequently, continuous centrifugation was conducted (JCF-Z Rotor, Beckman Inc.), whereupon 10 M sodium hydroxide was added to 50 liters of supernatant obtained to adjust the pH to 7.12, whereupon it was concentrated in a Pellicon cassette system (PTGC membrane, Millipore Corporation), and following replacement of buffer solution with 20 mM Tris/HCl (pH 8.0), was centrifuged(10,000 rpm for 30 minutes) to obtain supernatant. Subsequently, this supernatant was allowed to adsorb to DEAE-Toyopearl 650 M column (20 cmφ×84 cm, Tosoh Corporation) equilibrated with 20 mM Tris/HCl (pH 8.0), underwent a thorough wash, then eluted with 20 mM Tris/HCl containing 50 mM sodium chloride (pH 8.0), to obtain 95 liters of eluate as Met-hGH fractions. Further, this eluate was concentrated and desalted in a Pellicon cassette system (PTGC membrane, Millipore Corporation), then the buffer solution replaced with 20 mM Tris/HCl and 6 M urea (pH 8.0), to obtain 12.21 grams of Met-hGH.

EXAMPLE 3

Removal of N-terminal Methionine Residue (N-terminal Met)

To 1,800 milliliters of the Met-hGH solution obtained in Example 2, 450 milliliters of 2.5 M glyoxylic acid, 40 mM cupric sulfate, and 50% pyridine solution was added and stirred well, then allowed to react for 60 minutes at 25° C. This was subsequently allowed to apply to a Sephadex G-25 column (11.3 cmφ×125 cm, Pharmacia Biotech, Inc.) equilibrated with 20 mM Tris/HCl and 4.0 M urea (pH 8.0) at a flow rate of 3 liters/h, and developed using the same buffer solution as was used for equilibration, to obtain 4.2 liters of eluate as hGH fractions possessing a diketone of the methionine residue. This eluate was added into 20.8 liters of 1.2 M acetic acid, 2.4 M sodium formate, 3.6 M urea solution, and 48 mM 3,4-diaminobenzoic acid solution while stirring well, then allowed to react for 3 days at 30° C. while stirring slowly. Following the reaction, this solution was concentrated to 14 liters in a Pellicon cassette system (PTGC membrane, Millipore Corporation), then divided into 2 runs of 7 liters each to be applied at a flow rate of 6 liters/h to a Sephadex G-25 column (25.2 cmφ×50 cm, Pharmacia Biotech, Inc.) equilibrated with 20 mM Tris/HCl and 4.0 M urea (pH 8.0), to collect 20 liters of hGH fraction. Subsequently, via high speed liquid chromatography (Gilson HPLC system, Gilson Company, Inc.) this solution was subjected to flow adsorption in a DEAE-5PW column (21 cm×30 cm, Tosoh Corporation), then was eluted at a flow rate of 320 milliliters/minute for 70 minutes in a pH gradient of 70 to 85% B generated with A=50 mM Tris/HCl+2.5 M urea (pH 8.0) and B=50 mM MES [2-(N-morpholino)-ethane sulfonic acid]+2.5 M urea (pH 4.0), to obtain 5.84 liters of hGH fractions. To this hGH fraction, 16 milliliters of 10 M NaOH solution was added to adjust the pH to 7.1, whereupon high speed liquid chromatography (Gilson HPLC system, Gilson Company, Inc.) was conducted in 8 separate batches. Upon allowing the designated amount of the concentrate to flow through and adsorb to a POROS 20R1 column (5 cm×60 cm, Nihon PerSeptive Ltd.), elution was conducted at a flow rate of 50 milliliters/minute for 150 minutes in a pH gradient of 50 to 85% B generated with A=25% n-propanol+75% 50 mM Tris/HCl (pH 8.5) and B=35% n-propanol+65% 50 mM Tris/HCl (pH 8.5), to obtain 34.7 liters of eluate as hGH fraction. Distilled water was added to this eluate to dilute it to 200 liters, then following concentration to 5 liters in a Pellicon cassette system (PTGC membrane, Millipore Corporation), this solution was made to flow through and adsorb to a DEAE-SPW column (10.8 cm×20 cm, Tosoh Corporation) in 3 separate batches by high speed liquid chromatography (Gilson HPLC system, Gilson Company, Inc.), then eluted at a flow rate of 80 milliliters/minute for 70 minutes in a pH gradient of 70 to 85% generated with A=50 mM Tris/HCl+2.5 M urea (pH 8.0) and B=50 mM MES [2-(N-morpholino)-ethane sulfonic acid]+2.5 M urea (pH 4.0), to obtain 1,616 milliliters of hGH fraction. To this hGH fraction, 2 milliliters of 10 M NaOH solution was added to adjust the pH to 7.1, followed by concentration with an ultrafilter (Omega membrane, Fuji Filter Mfg. Co., Ltd.) to obtain 0.4 liters of concentrate. This concentrate was made to flow through a Sephacryl S-100 column (11.3 cmφ×50 cm, Pharmacia Biotech, Inc.) at a flow rate of 2 liters/h, and developed to obtain hGH fraction. Further, this solution was filtered through a Millipack 60 (Millipore Corporation) to obtain 2,391 milliliters of hGH solution (4,638 milligrams of hGH).

EXAMPLE 4

Characterization of hGH (a) Analysis Using SDS Polyacrylamide Gel Electrophoresis To the hGH obtained in Example 3, an equal volume of sample buffer containing 100 mM DTT [Laemmli, Nature, 227, 680 (1979)] was added and stirred well, followed by heating for 2 minutes at 95° C., whereupon electrophoresis was performed using Multigel 10/20 (Daiichi Pure Chemicals Co., Ltd.). Following electrophoresis, the gel was stained with Coomassie Brilliant Blue, whereupon a single band was observed at approximately 22 KDa, thereby confirming that the purified hGH was monomeric (FIG. 1).

(b) N-terminal Amino Acid Sequence Analysis

The N-terminal amino acid sequence was determined using a gas phase protein sequencer (Perkin Elmer Applied Biosystems Model 477A). The hGH N-terminal amino acid sequence thus obtained matched the hGH N-terminal amino acid sequence that was deduced from the cDNA base sequence (Table 1).

TABLE 1

| Residue No. | PTH[1] Amino acid detected (pmol) | Amino acid deduced from hGH base sequence |
|---|---|---|
| 1 | Phe (848) | Phe |
| 2 | Pro (520) | Pro |
| 3 | Thr (403) | Thr |
| 4 | Ile (620) | Ile |
| 5 | Pro (401) | Pro |
| 6 | Leu (429) | Leu |
| 7 | Ser (92) | Ser |
| 8 | Arg (262) | Arg |
| 9 | Leu (376) | Leu |
| 10 | Phe (283) | Phe |
| 11 | Asp (182) | Asp |
| 12 | Asn (175) | Asn |
| 13 | Ala (175) | Ala |
| 14 | Met (194) | Met |
| 15 | Leu (261) | Leu |
| 16 | Arg (181) | Arg |
| 17 | Ala (144) | Ala |
| 18 | His (80) | His |
| 19 | Arg (152) | Arg |
| 20 | Leu (200) | Leu |
| 21 | His (71) | His |

[1]Phenylthiohydantoin

Analysis was performed using 1 nmol.

(c) Amino Acid Composition Analysis

The amino acid composition was determined using an amino acid analyzer (L-8500A, Hitachi, Ltd.). The hGH amino acid composition thus obtained matched the amino acid composition deduced from the cDNA base sequence (Table 2).

TABLE 2

| Amino acid | Number of residues per mole | Value deduced from hGH base sequence |
|---|---|---|
| Asx | 19.8 | 20 |
| Thr[1)] | 9.7 | 10 |
| Ser[1)] | 16.1 | 18 |
| Glx | 27.0 | 27 |
| Pro | 7.7 | 8 |
| Gly | 8.0 | 8 |
| Ala | 6.9 | 7 |
| Cys[2)] | N.D. | 4 |
| Val | 6.8 | 7 |
| Met | 2.9 | 3 |
| Ile | 7.4 | 8 |
| Leu | 26.6 | 26 |
| Tyr | 7.9 | 8 |
| Phe | 12.4 | 13 |
| His | 3.0 | 3 |
| Lys | 8.7 | 9 |
| Arg | 10.7 | 11 |
| Trp | 0.9 | 1 |

Acid hydrolysis (mean value of 24-hours and 48-hour hydrolysis, at 110° C., with 6N HCl - 4% thioglycolic acid)
[1)]Value extrapolated at 0 hours.
[2)]Not detected.

Analysis was performed using approximately 10 μg.

(d) C-terminal Amino Acid Analysis

The C-terminal amino acid was determined using an amino acid analyzer (L-8500A, Hitachi, Ltd.). The hGH C-terminal amino acid thus obtained matched the C-terminal amino acid deduced from the cDNA base sequence (Table 3).

TABLE 3

| C-terminal amino acid | Recovery rate (%) |
|---|---|
| Phe | 94 |

Phase hydrazinolysis (at 100° C. for 6 hours)
Analysis performed using 20 nmol.

EXAMPLE 5

Measurement of hGH Activity

The growth promoting activity of the purified hGH obtained in Example 3 on Nb2 cells [Journal of Clinical Endocrinology and Metabolism, Vol. 51, p. 1058 (1980)] was equivalent to that of the reference material (Chemicon International, Inc., Temecula, Calif., USA).

EXAMPLE 6

Removal of N-terminal Met 20 mM Tris/HCl and 4.0 M urea (pH 8.0) was added to 0.4 milliliters of hGH fraction possessing diketone of the methionine residue obtained in Example 3, to dilute it to 2 milliliters. An equal volume of 4 M acetic acid, 4 M sodium acetate, 6 M urea solution, and 80 mM N-methyl-1,2-phenylenediamine solution was added to said solution, stirred well, and was allowed to react for 20 hours at 30° C. Following the reaction, the solution was applied to a Sephadex G-25 column (1 cmφ×30 cm, Pharmacia Corporation) equilibrated with 20 mM Tris/HCl and 4.0 M urea (pH 8.0) at a flow rate of 60 milliliters/h, to collect 10 milliliters of hGH fraction. Subsequently, by high speed liquid chromatography (Gilson HPLC system, Gilson Company, Inc.), this solution was applied to a DEAE-5PW column (2.15 cm×15 cm, Tosoh Corporation) and made to flow through and adsorb, followed by elution at a flow rate of 7.5 milliliters/minute for 70 minutes in a pH gradient of 70 to 85% B generated with A=50 mM Tris/HCl+2.5 M urea (pH 8.0) and B=50 mM MES [2-(N-morpholino)-ethane sulfonic acid]+2.5 M urea (pH 4.0), to obtain hGH.

EXAMPLE 7

Removal of N-terminal Met 20 mM Tris/HCl and 4.0 M urea (pH 8.0) was added to 0.4 milliliters of hGH fraction possessing diketone of the methionine residue obtained in Example 3, to dilute it to 2 milliliters. An equal volume of 2 M acetic acid, 4 M sodium formate, 6 M urea solution, and 80 mM N-methyl-1,2-phenylenediamine solution was added to this diluent, stirred well, and allowed to react for 20 hours at 30° C. After the reaction, the solution was applied to a Sephadex G-25 column (1 cmφ×30 cm, Pharmacia Corporation) equilibrated with 20 mM Tris/HCl and 4.0 M urea (pH 8.0) at a flow rate of 60 milliliters/h, to collect 10 milliliters of hGH fraction. Subsequently, in high speed liquid chromatography (Gilson HPLC system, Gilson Company, Inc.), this solution was applied to a DEAE-SPW column (2.15 cm×15 cm, Tosoh Corporation) and made to flow through and adsorb, followed by elution at a flow rate of 7.5 milliliters/minute for 70 minutes in a pH gradient of 70 to 85% B generated with A=50 mM Tris/HCl+2.5 M urea (pH 8.0) and B=50 mM MES [2-(N-morpholino)-ethane sulfonic acid]+2.5 M urea (pH 4.0), to obtain hGH.

EXAMPLE 8

Removal of N-terminal Met

To 1.8 ml of the Met-hGH solution obtained in Example 2, 0.45 ml of 2.5 M glyoxylic acid, 40 mM cupric sulfate, and 50% pyridine solution was added and, after stirring well, was allowed to react for 60 minutes at 25° C. This was subsequently applied at a flow rate of 100 ml/h to a Sephadex G-25 column (1.5 cmφ×30 cm, Pharmacia Biotech, Inc.) equilibrated with 20 mM Tris/HCl and 4.0 M urea (pH 8.0), and developed using the same buffer solution as was used for equilibration, to obtain 10 ml of eluate as hGH fractions possessing diketone of the methionine residue. This eluate was added into 49.5 ml of 1.2 M acetic acid, 2.4 M sodium formate, 3.6 M urea solution, and 48 mM 3,4-diaminobenzoic acid solution while stirring well, then allowed to react for 24 hours at 37° C. while stirring slowly. Following the reaction, it was then applied at a flow rate of 500 ml/h to a Sephadex G-25 column (4.6 cmφ×60 cm, Pharmacia Biotech, Inc.) equilibrated with 20 mM Tris/HCl and 4.0 M urea (pH 8.0), to collect 150 ml of hGH fractions. Subsequently, in high speed liquid chromatography (Gilson HPLC system, Gilson Company, Inc.) this solution was made to flow through and adsorb to a DEAE-5PW column (2.15 cm×15 cm, Tosoh Corporation), followed by elution at a flow rate of 7.5 ml/minute for 70 minutes in a pH gradient of 70 to 85% B generated with A 50 mM Tris/HCl+2.5 M urea (pH 8.0) and B=50 mM MES [2-(N-morpholino)-ethane sulfonic acid]+2.5 Murea (pH 4.0), to obtain 6.7 mg of hGH fractions.

EXAMPLE 9

Removal of N-terminal Met 0.45 ml of 2.5 M glyoxylic acid, 40 mM cupric sulfate, and 50% pyridine solution was added to 1.8 ml of the Met-hGH solution obtained in Example 2, stirred well, and was allowed to react for 60 minutes at 25° C. This was subsequently applied at a flow rate of 100 ml/h to a Sephadex G-25 column (1.5 cmφ×30 cm, Pharmacia Biotech, Inc.) equilibrated with 20 mM Tris/HCl and 4.0 M urea (pH 8.0), and developed using the same buffer solution as was used for equilibration, to obtain 10 ml of eluate as hGH fractions possessing diketone of the methionine residue. This eluate was added into 10 ml of 2 M formic acid, 10 M sodium formate, 6 M urea solution, and 80 mM 3,4-diaminobenzoic acid solution while stirring well, then allowed to react for 3 days at 30° C. while stirring slowly. Following the reaction, it was then applied at a flow rate of 500 ml/h to a Sephadex G-25 column (4.6 cmφ×60 cm, Pharmacia Biotech, Inc.) equilibrated with 20 mM Tris/HCl and 4.0 M urea (pH 8.0), to collect 100 ml of hGH fractions. Subsequently, in high speed liquid chromatography (Gilson HPLC system, Gilson Company, Inc.) this solution was made to flow through and adsorb to a DEAE-5PW column (2.15 cm×15 cm, Tosoh Corporation), followed by elution at a flow rate of 7.5 ml/minute for 70 minutes in a pH gradient of 70 to 85% B generated with A=50 mM Tris/HCl+2.5 M urea (pH 8.0) and B=50 mM MES [2-(N-morpholino)-ethane sulfonic acid]+2.5 M urea (pH 4.0), to obtain 6.0 mg of hGH fractions.

EXAMPLE 10

Activation of 20K-hGH Possessing Methionine Residue (Met-20K-hGH)

40 g of cells obtained via the method described in Reference 2 of Unexamined Kokai Application Heisei 10-234386 was suspended in 100 milliliters of PBS (phosphate buffered saline), then the cells were disrupted with 5 minutes of sonication on a sonifier (Branson Ultrasonics corporation). The lysate was subjected to centrifugation (10,000 rpm for 20 minutes) and the supernatant was discarded, to obtain the pellet. Following the addition of 2 liters of 50 mM Tris/HCl and 8 M guanidine hydrochloride solution (pH 8.0) to the pellet to dissolve it, centrifugation (10,000 rpm for 120 minutes) was performed. 24 liters of 50 mM Tris/HCl, 0.2B mM GSSG, 1.4 mM GSH, and 0.7 M arginine (pH 8.0) was added to 2 liters of supernatant obtained, whereupon activation was conducted for 1 day at 4° C.

EXAMPLE 11

Purification of Met-20K-hGH

The solution which underwent activation obtained in Example 10 was desalted and concentrated in a Minitan ultrafiltration system (PTGC membrane, Millipore Corporation) while adding 20 mM Tris/HCl and 2.5 M urea (pH 8.0) until the electric conductivity was no greater than 10 mS/cm, whereupon the concentrate obtained was subjected to centrifugation (10,000 rpm for 20 minutes), to yield 150 milliliters of supernatant. Subsequently, this supernatant was applied to a HiLoad™ Q Sepharose 16/10 HP column (1.6 cmφ×10 cm, Pharmacia Biotech, Inc.) equilibrated with 50 mM Tris/HCl and 2.5 M urea/10% acetonitrile (pH 8.2) for adsorption, then underwent a thorough wash, followed by elution at a flow rate of 3.0 milliliters/minute with a sodium chloride gradient from 0 to 0.18 M, to obtain 28 milliliters of eluate as Met-20K-hGH fractions. These fractions were further concentrated and desalted using a Centriplus-10 (Millipore Corporation) to yield 15 milliliters of concentrate. This liquid was readsorbed onto a HiLoad™ Q Sepharose 16/10 HP column (1.6 cmφ×10 cm, Pharmacia Biotech, Inc.) equilibrated with 50 mM Tris/HCl and 2.5 M urea/10% acetonitrile (pH 8.2), and underwent a thorough washing, followed by elution at a flow rate of 3.0 milliliters/minute for 60 minutes in a pH gradient of 0 to 100% B generated with A=50 mM Tris/HCl, 2.5 M urea, and 10% acetonitrile (pH 8.2) and B=50 mM MES [2-(N-morpholino)-ethane sulfonic acid], 2.5 M urea, and 10% acetonitrile (pH 4.0), to obtain 12 milliliters of Met-20K-hGH fractions. To this eluate, 0.6 milliliters of 2 M Tris/HCl (pH 7.8) was added to adjust the pH to 7.2, followed by concentration using a Centriplus-10 (Millipore Corporation). 0.5 milliliters of this concentrate was added to a Superdex™ 75 HR 10/30 (1.0 cmφ×30 cm, Pharmacia Biotech, Inc.) equilibrated with PBS containing 10% ethanol, to obtain 7.5 milliliters of Met-20K-hGH fractions.

EXAMPLE 12

Removal of N-terminal Met 6 milliliters of the Met-20K-hGH solution obtained in Example 11 was applied to a Sephadex G-25 column (10 mm ID×30 cm, Pharmacia Biotech, Inc.) equilibrated with 20 mM Tris/HCl and 8 M urea (pH 8.0) and the eluted Met-20K-hGH fractions were collected, followed by further concentration to 2 milliliters using an ultrafiltration system (Diaflow Membrane YM10, 25 mm, Amicon, Inc.). 0.5 milliliters of 2.5 M glyoxylic acid, 40 mM cupric sulfate, and 50% pyridine solution was added to this solution, stirred well, and allowed to react for 60 minutes at 25° C. Subsequently, this reaction solution was applied to a Sephadex G-25 column (10 mm ID×40 cm, Pharmacia Biotech, Inc.) equilibrated with 20 mM Tris/HCl and 4 M urea (pH 8.0) to collect 4 milliliters of eluate as 20K-hGH fractions possessing diketone of methionine residue. 20 milliliters of 1.2 M acetic acid, 2.4 M sodium formate, 3.6 M urea, and 48 M 3,4-diaminobenzoic acid was added to this solution, stirred well, and was allowed to react for 65 hours at 300C. Following the reaction, the reaction product was applied to a Sephadex G-25 column (20 mm ID×40 cm, Pharmacia Biotech, Inc.) equilibrated with 20 mM Tris/HCl and 4 M urea (pH 8.0), to collect 20K-hGH fractions, whereupon high speed liquid chromatography (Gilson HPLC system, Gilson Company, Inc.) was conducted, wherein the fractions were applied to a HiLoad™ Q Sepharose 16/10 HP column (1.6 cmφ×10 cm, Pharmacia Biotech, Inc.) equilibrated with 50 mM Tris/HCl and 2.5 M urea/10% acetonitrile (pH 8.2) for adsorption, and made to undergo a thorough wash, followed by elution at a flow rate of 3.0 milliliters/minute for 60 minutes in a pH gradient of 0 to 100% generated with A=50 mM Tris/HCl, 2.5 M urea, and 10% acetonitrile (pH 8.2), and B 50 mM MES [2-(N-morpholino)-ethane sulfonic acid), 2.5 M urea, and 10% acetonitrile (pH 4.0), to obtain 12 milliliters of 20K-hGH fractions. 0.6 milliliters of 2 M Tris/HCl (pH 7.8) was added to this eluate to adjust the pH to 7.2, whereupon it was concentrated using a Centriplus-10 (Millipore Corporation). 0.5 milliliters of this concentrate was added to a Superdex™ 75 HR 10/30 (1.0 cmφ×30 cm, Pharmacia Biotech, Inc.) equilibrated with PBS containing 10% ethanol, followed by elution with PBS containing 10% ethanol to obtain 7.5 milliliters of 20K-hGH fractions.

EXAMPLE 13

Characterization of 20K-hGH (a) N-terminal Amino Acid Sequence Analysis

The N-terminal amino acid sequence was determined using a gas phase protein sequencer (Perkin Elmer Applied Biosystems Model 477A). The 20K-hGH N-terminal amino acid sequence thus obtained matched the 20K-hGH N-terminal amino acid sequence that was deduced from the cDNA base sequence (Table 4).

TABLE 4

| Residue No. | PTH[1] Amino acid detected (pmol) | Amino acid deduced from 20K-hGH base sequence |
| --- | --- | --- |
| 1 | Phe (642) | Phe |
| 2 | Pro (504) | Pro |
| 3 | Thr (342) | Thr |
| 4 | Ile (410) | Ile |
| 5 | Pro (200) | Pro |
| 6 | Leu (378) | Leu |
| 7 | Ser (95) | Ser |
| 8 | Arg (170) | Arg |
| 9 | Leu (285) | Leu |
| 10 | Phe (262) | Phe |

[1]Phenylthiohydantoin
Analysis performed using 1 nmol.

(b) Amino Acid Composition Analysis

The amino acid composition was determined using an amino acid analyzer (System 6300, Beckman, Inc.). The amino acid composition of the 20K-hGH obtained in Example 12 matched the amino acid composition deduced from the cDNA base sequence of 2OK-hGH (Table 5).

TABLE 5

| Amino acid | Number of residues per mole | Value deduced from 20K-hGH base sequence |
| --- | --- | --- |
| Asx | 20.2 | 20 |
| Thr[1] | 9.7 | 10 |
| Ser[1] | 16.5 | 17 |
| Glx | 22.0 | 22 |
| Pro | 6.9 | 7 |
| Gly | 8.0 | 8 |
| Ala | 6.2 | 6 |
| Cys[2] | N.D. | 4 |
| Val | 7.0 | 7 |
| Met | 2.9 | 3 |
| Ile | 6.5 | 7 |
| Leu | 24.3 | 25 |
| Tyr | 5.9 | 6 |
| Phe | 12.2 | 12 |
| His | 3.1 | 3 |
| Lys | 7.1 | 7 |
| Arg | 10.7 | 11 |
| Trp | N.D. | 1 |

Acid hydrolysis (mean value of 24-hours and 48-hour hydrolysis, at 110° C., with 6N HCl-1% phenol). Analysis was performed using approximately 20 μg.
[1]Value extrapolated at 0 hours.
[2]Not detected.

EXAMPLE 14

Measurement of 20K-hGH Activity

The growth promoting activity of the 20K-hGH obtained in Example 12 on Nb2 cells [Journal of Clinical Endocrinology and Metabolism, Vol. 51, p. 1058 (1980)] was confirmed.

EXAMPLE 15

Manufacture of Human BTC which Possesses Methionine Residue (Human Met-BTC)

In accordance with Examples 4 through 6, 8, and 13 of Unexamined Kokai Application Heisei 6-87894 (EP-A-0555785), human Met-BTC was manufactured in the following method.

(Construction of Human BTC cDNA Expression Plasmid in E. coli)

The 0.6 Kb EcoRI-BamHI fragment, which codes for human pro-BTC (1–147 amino acid residue), was isolated from Plasmid pTB 1515 described in Example 5 of Unexamined Kokai Application Heisei 6-87894 (EP-A-0555785). Upon ligating a synthetic adapter with ATG translation initiation codon (5'-TATGGATGGG-3' (SEQ ID NO: 7); 5'-AATTCCCATCCA-3' (SEQ ID NO: 8)) into the EcoRI site of the 0.6 Kb fragment, the 0.6 Kb NdeI-BamHI fragment generated was inserted into plasmid pET-3c containing a T7 promoter (Gene, Vol. 56, p. 125 (1987)), to construct plasmid pTB1505.

Figure 2:
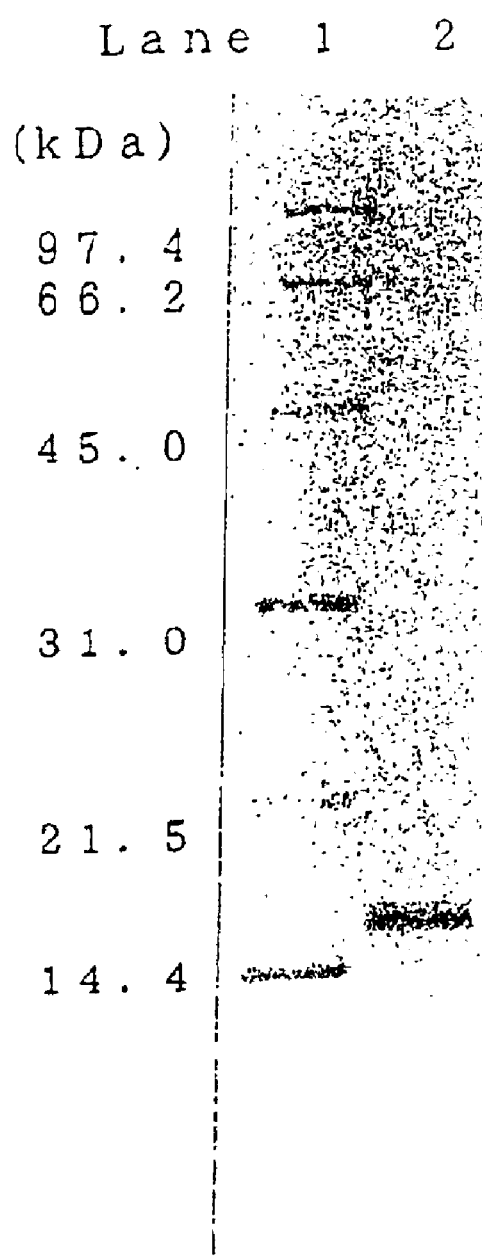
FIG. 2 is an illustration of the results of electrophoresis obtained in Example 16a). Lane 1 represents the molecular weight marker, while Lane 2 represents the BTC obtained in Example 15.

In order to obtain DNA fragments that code for the 80 amino acid residues in human BTC (1 (Asp) through 80 (Tyr) in FIGS. 10-1 and 10-2 (Unexamined Kokai Application Heisei 6-87894 (EP-A-0555785)), PCR (polymerase chain reaction) was performed using plasmid pTB1505 as the template and two oligonucleotides (5'-ATACATATGGATGGGAATTCCA-3' (SEQ ID NO: 9); 5'-CCGGATCCTAGTAAAACAAGTCAACTCT-3' (SEQ ID NO: 10)) as the primer. The product was digested with NdeI and BamHI, followed by fractionation via electrophoresis with 2.0% agarose gel, to isolated the targetted 0.25 Kb DNA fragment. This 0.25 Kb NdeI-BamHI fragment was ligated to the downstream of the T7 promoter of pET-3c using T4DNA ligase, to obtain plasmid pTB1516 (See FIG. 13 of Unexamined Kokai Application Heisei 6-87894(EP-A-0555785)).

(Expression of Human Met-BTC in E. coli)

E. coli MM294 was lysogenized by a recombinant lambda-phage containing the T7 RNA polymerase gene (Studier, supra). Subsequently, plasmid pLysS was introduced into this E. coli MM294(DE3), to obtain E. coli MM294(DE3)/pLysS. The plasmid pTB1516 obtained in the aforementioned Reference was introduced into these cells, to obtain E. coli MM294(DE3)/pLysS, pTB1516.

This transformant was cultured with shaking for 8 hours at 37° C., in a 2 liter flask containing 1 liter of LB culture medium (1% peptone, 0.5% yeast extract, 0.5% sodium chloride) containing 50 μg/ml of ampicillin and 15 μg/ml of chloramphenicol. The culture solution thus obtained was transferred to a 50 liter fermenter containing 19 liters of fermentation medium (1.68% dibasic sodium phosphate, 0.3% monobasic potassium phosphate, 0.1% ammonium chloride, 0.05% sodium chloride, 0.05% magnesium sulfate, 0.02% defoaming agent, 0.00025% ferrous sulfate, 0.0005% thiamine hydrochloride, 1.5% glucose, 1.5% casamino acid), to start aeration/agitation at 30° C. When the turbidity of the culture solution reached approximately 500 Klett units, 100 mg/liter of isopropyl-β-D-thiogalactopyranoside (IPTQ) was added; and cultivation was continued, to be terminated 7 hours later. This culture solution was subjected to centrifugation to obtain approximately 340 g of wet cells, which were then frozen for storage at −80° C.

This transformed E. coli (MM294(DE3)/pLysS, pTB1516) was deposited with the National Institute of Bioscience and Human-Technology of the Agency of Industrial Science and Technology of the Ministry of International Trade and Industry (NIBH) on Apr. 21, 1992, under accession number FERM BP-3836, and with the Institution for Fermentation, Osaka (IFO) on Apr. 16, 1992, under accession number IFO 15282.

Upon dissolving 10 mg of the human β-cellulin possessing N-terminal methionine residue (Met-BTC), obtained via the aforementioned method, in 4 ml of 3M urea solution, a mixture of 0.25 ml 80 mM cupric sulfate, 0.25 g glyoxylic acid, and 0.5 ml pyridine was added, to be allowed to react for 1 hour at 25° C. Upon completion of the reaction, the reaction solution was applied to a Sephadex G-25 column (25 mm ID×600 mmL) equilibrated with 2.5 M urea+50 mM phosphate buffer solution (pH 6.0), developed in the solution used for equilibration at a flow rate of 6 ml/minute, and the BTC fractions possessing diketone of the methionine residue were pooled. Subsequently, an equal volume of 2 M acetic acid, 4 M sodium formate, and 3 M urea solution was added to these fractions, followed by the addition of 3,4-diaminobenzoic acid so that the concentration was 40 mM, whereupon deaeration was conducted and a nitrogen gas seal applied, to allowed reaction to proceed for 5 days at 25° C. Upon completion of the reaction, the reaction solution was applied to a Sephadex G-25 column (46 mm ID×600 mmL) equilibrated with 50 mM phosphate buffer solution (pH 6.0), developed in the buffer solution used for equilibration at a flow rate of 10 ml/minute, and the BTC fractions which do not possess N-terminal methionine pooled. The pooled fractions, upon being adjusted to pH 6.0, were adsorbed to a CM-5PW (21.5 mm ID×150 mmL, Tosoh Corporation) equilibrated with 50 mM phosphate buffer solution+0.1 M NaCL+2.5 M urea (pH 5.0) to be eluted at a flow rate of 6 ml/minute for 60 minutes at a step gradient of 0 to 100% B (B=50 mM boric-acid buffer solution+0.1 M NaCl+2.5 M urea, pH 9.0), and the BTC fractions pooled. The BTC fractions were further adsorbed onto a C4P-50 (10 mm ID×250, mmL, Showa Denko K.K.) equilibrated with 0.1% TFA, then eluted at a flow rate of 2 ml/minute for 40 minutes on a step gradient of 20 to 60% B (B=80% acetonitrile/0.1% TFA). Following pooling, the BTC fractions were lyophilized, to yield approximately 2.6 mg of BTC.

EXAMPLE 16

Characterization of BTC a) Analysis Using SDS Polyacrylamide Gel Electrophoresis The BTC obtained in Example 15 was suspended in sample buffer [Laemmli, Nature, 227, 680 (1970)] and heated for 1 minute at 100° C., followed by electophresis using Multigel 15/25 (Daiichi Pure chemicals Co., Ltd.). Following electrophoresis, the gel was stained with Coomassie Brilliant Blue, whereupon a single band of protein was observed, thereby confirming that the purified product was virtually monomeric (FIG. 2).

b) N-terminal Amino Acid Sequence Analysis

The N-terminal amino acid sequence was determined using a gas phase protein sequencer (Perkin Elmer Applied Biosystems Model 477A). The amino acid sequence of BTC thus obtained matched the BTC N-terminal amino acid sequence that was deduced from the BTC cDNA base sequence (Table 6).

TABLE 6

| Residue No. | PTH[1] Amino acid detected (pmol) | Amino acid (pmol) deduced from BTC base sequence |
|---|---|---|
| 1 | Asp (261) | Asp |
| 2 | Gly (457) | Gly |
| 3 | Asn (300) | Asn |
| 4 | Ser (107) | Ser |
| 5 | Thr (75) | Thr |
| 6 | Arg (181) | Arg |
| 7 | Ser (121) | Ser |

TABLE 6-continued

| Residue No. | PTH[1] Amino acid detected (pmol) | Amino acid (pmol) deduced from BTC base sequence |
|---|---|---|
| 8 | Pro (245) | Pro |
| 9 | Glu (55) | Glu |
| 10 | Thr (71) | Thr |
| 11 | Asn (133) | Asn |
| 12 | Gly (149) | Gly |
| 13 | Leu (132) | Leu |
| 14 | Leu (155) | Leu |
| 15 | N.D. | Cys |
| 16 | Gly (111) | Gly |
| 17 | Asp (70) | Asp |
| 18 | Pro (65) | Pro |
| 19 | Glu (29) | Glu |
| 20 | Glu (64) | Glu |

Analysis was performed using 1 nmol.
N.D.: Not detected
[1]Phenylthiohydantoin c) Amino Acid Composition Analysis The amino acid composition was determined using an amino acid analyzer (Beckman System 6300E). The amino acid composition obtained matched the amino acid composition deduced from the BTC CDNA base sequence (Table 7).

TABLE 7

| Amino acid | Number of residues per mole | Value deduced from BTC base sequence |
|---|---|---|
| Asx | 7.0 | 7 |
| Thr[1] | 6.1 | 6 |
| Ser[1] | 4.8 | 5 |
| Glx | 9.3 | 9 |
| Pro | 3.8 | 4 |
| Gly | 7.1 | 7 |
| Ala | 4.0 | 4 |
| Cys[2] | N.D. | 8 |
| Val | 3.9 | 4 |
| Met | 0 | 0 |
| Ile | 1.9 | 2 |
| Leu | 3.0 | 3 |
| Tyr | 3.7 | 4 |
| Phe | 3.3 | 3 |
| His | 2.3 | 2 |
| Lys | 5.0 | 5 |
| Arg | 6.9 | 7 |
| Trp | 0 | 0 |

Acid hydrolysis (mean value of 24-hours and 48-hour hydrolysis, at 110° C., with 6N hydrochloric acid and 1% phenol).
[1]Value extrapolated at 0 hours.
[2]Not detected
Analysis was performed using ca 20 μg.

d) C-terminal Amino Acid Analysis

The C-terminal amino acid was determined using an amino acid analyzer (Beckman System 6300E). The BTC thus obtained matched the C-terminal amino acid deduced from the cDNA base sequence (Table 8).

TABLE 8

| C-terminal amino acid analysis | | |
|---|---|---|
| BTC | C-terminal amino acid | Recovery rate (%) |
| | Tyr | 44.6 |

Phase hydrazinolysis (at 100° C. for 3.5 hours)
Analysis was performed using 15 nmol.

e) Biological Activity of BTC

The purified product was measured for activity according to the method described in Molecular Cell Biology, 8, 588 (1988) using BALB/C3T3 A31-714 Clone 4 (International Journal of Cancer, 12, 463 (1973), whereupon the activity of said product was confirmed to be equivalent to that of the reference material.

EXAMPLE 17

Upon dissolving 50 mg of human interleukin-2 possessing N-terminal methionine residue (Met-IL-2), obtained according to the method in Reference 5 of Unexamined Kokai Application Heisei 10-72489 (EP-A-812856), into 40 ml of 4 M urea solution, a mixture of 2.5 ml 100 mM cupric sulfate, 2.5 g glyoxylic acid, and 5.0 ml pyridine was added, to be allowed to react for 1 hour at 25° C. After the reaction, the reaction solution was applied to a Sephadex G-25 column (46 mm ID×600 mmL) equilibrated with 10 mM phosphate buffer solution+2.5 M urea (pH 5.0), developed in the buffer used for equilibration at a flow rate of 10 ml/minute, and IL-2 fractions possessing diketone of the methionine residue were pooled. Subsequently, an equal volume of 2 M acetic acid, 4 M sodium formate, and 3 M urea solution was added to these fractions, followed by the addition of 3,4-diaminobenzoic acid to make the concentration 40 mM, whereupon deaeration was conducted and a nitric gas seal was applied, and the reaction allowed to proceed for 5 days at 25° C. Upon completion of the reaction, the reaction solution was applied to a Sephadex G-25 column (46 mm ID×600 mmL) equilibrated with 10 mM phosphate buffer solution+2.5 M urea (pH 5.0), developed in the buffer solution used for equilibration at a flow rate of 10 ml/minute, and IL-2 fractions which do not possess N-terminal methionine pooled. The pooled IL-2 fractions were adsorbed onto SP-5PW (21.5 mm ID×150 mmL, Tosoh Corporation) equilibrated with 25 mM phosphate buffer solution (pH 7.0), followed by elution at a flow rate of 6 ml/minute for 60 minutes on a step gradient of 30 to 80% B (B 25 mM phosphate buffer solution, pH 8.0), to yield 17.3 mg of IL-2 fractions.

EXAMPLE 18

Characterization of IL-2 a) Analysis Using SDS Polyacrylamide Gel Electrophoresis

Figure 3:
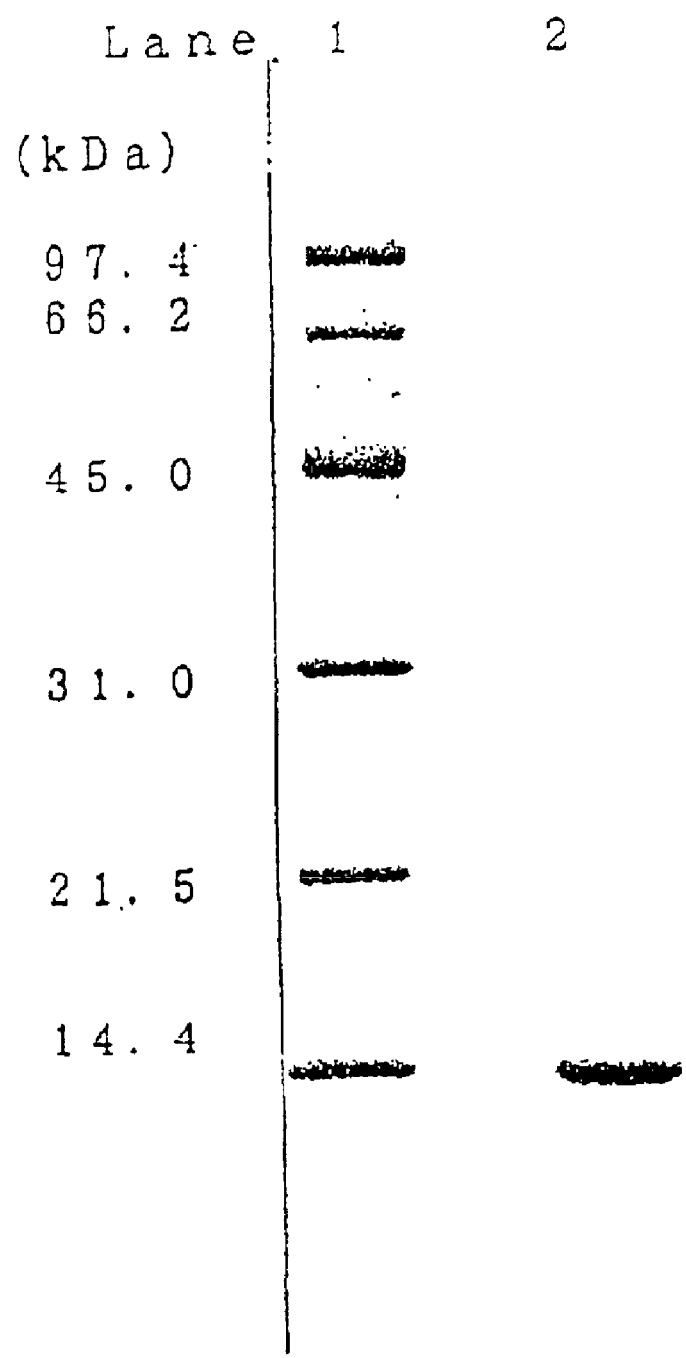
FIG. 3 is an illustration of the results of electrophoresis obtained in Example 18a). Lane 1 represents the molecular weight marker, while Lane 2 represents the IL-2 obtained in Example 17.

The IL-2 obtained in Example 17 was suspended in the sample buffer. Laemmli, Nature, 227, 680 (1970)] and heated for 1 minute at 100° C., followed by electrophoresis using Multigel 15/25 (Daiichi Pure Chemicals Co., Ltd.). Following electrophoresis, the gel was stained with Coomassie Brilliant Blue, whereupon a single band of protein was observed, thereby confirming that the purified product was virtually monomeric (FIG. 3).

b) N-terminal Amino Acid Sequence Analysis

The N-terminal amino acid sequence was determined using a gas phase protein sequencer (Perkin Elmer Applied Biosystems Model 477A). The amino acid sequence of IL-2 thus obtained matched the IL-2 N-terminal amino acid sequence that was deduced from the IL-2 cDNA base sequence (Table 9).

TABLE 9

| Residue No. | PTH[1]) Amino acid detected (pmol) | Amino acid deduced from IL-2 base sequence |
|---|---|---|
| 1 | Ala (701) | Ala |
| 2 | Pro (354) | Pro |
| 3 | Thr (359) | Thr |
| 4 | Ser (122) | Ser |
| 5 | Ser (128) | Ser |
| 6 | Ser (78) | Ser |
| 7 | Thr (46) | Thr |
| 8 | Lys (176) | Lys |
| 9 | Lys (61) | Lys |
| 10 | Thr (40) | Thr |

Analysis was performed using 1 nmol.
[1])Phenylthiohydantoin c) Amino Acid Composition Analysis The amino acid composition was determined using an amino acid analyzer. (Beckman System 6300E). The amino acid composition obtained matched the amino acid composition deduced from the IL-2 CDNA base sequence (Table 10).

TABLE 10

| Amino acid | Number of residues per mole | Value deduced from IL-2 base sequence |
|---|---|---|
| Asx | 11.8 | 12 |
| Thr[1]) | 12.9 | 13 |
| Ser[1]) | 7.0 | 8 |
| Glx | 18.4 | 18 |
| Pro | 4.8 | 5 |
| Gly | 2.0 | 2 |
| Ala | 4.8 | 5 |
| Cys[2]) | N.D. | 3 |
| Val | 3.5 | 4 |
| Met | 3.8 | 4 |
| Ile | 7.7 | 9 |
| Leu | 22.0 | 22 |
| Tyr | 2.8 | 3 |
| Phe | 5.6 | 6 |
| His | 2.9 | 3 |
| Lys | 10.3 | 11 |
| Arg | 3.7 | 4 |
| Trp | 0.9 | 1 |

Acid hydrolysis (mean value of 24-hours and 48-hours hydrolysis, at 110° C., with 6N hydrochloric acid - 4% thioglycolic acid).
[1])Value extrapolated at 0 hours.
[2])Not detected d) C-terminal Amino Acid Analysis The C-terminal amino acid was determined using an amino acid analyzer (Beckman System 6300E). The IL-2 thus obtained matched the C-terminal amino acid deduced from the cDNA base sequence (Table 11).

TABLE 11

| | C-terminal amino acid analysis | |
|---|---|---|
| IL-2 | C-terminal amino acid | Recovery rate (%) |
| | Thr | 32.5 |

Phase hydrazinolysis (at 100° C. for 3.5 hours)
Analysis was performed using 15 nmol.

e) Biological Activity of IL-2

Measurement of biological activity was performed according to the method using IL-2 dependent cells described by Hinuma et al. [Biochem. Biophys. Res. Commun., 109, 363 (1982)], whereupon the biological

EXAMPLE 19

Activation of Met-hGH 4 liters of 50 mM Tris/acetic acid, 8 M guanidine hydrochloride solution (pH 8.5) was added to 1 kg of the cells obtained in Reference 2 to dissolve the cells, followed by centrifugation (10,000 rpm). 44 liters of 50 mM Tris/acetic acid, 1.09 mM reduced glutathione, 0.055 mM oxidized glutathione, 109 mM arginine, and 4.36 M urea solution (pH 8.0) was added to approximately 4 liters of supernatant obtained, and the activation was allowed to proceed for 3 days at 4° C. Following the activation, the solution was concentrated and desalted in a Pellicon cassette system (Biomax 8 membrane, Millipore Corporation) while adding approximately 25 liters of 20 mM Tris/acetic acid and 2.5 M urea solution (pH 8.0), until the electrical conductivity was no greater than 5 mS/cm. Subsequently, desalting was conducted again while adding approximately 35 liters of 20 mM Tris/acetic acid solution (pH 8.0), followed by centrifugation (10,000 rpm) to obtain supernatant. Subsequently, the supernatant was adsorbed onto a DEAE-Toyopearl 650 M column (30 cm$\phi$×60 cm, Tosoh Corporation) equilibrated with 20 mM Tris/acetic acid solution (pH 8.0), then thoroughly washed in 20 mM Tris/acetic acid solution (pH 8.0) and 20 mM Tris/acetic acid, 25 mM sodium chloride solution (pH 9.0), followed by elution with 20 mM Tris/acetic acid and 55 mM sodium chloride solution (pH 8.0), to obtain 50 liters of eluate as Met-hGH fractions. This eluate was concentrated and desalted in a Pellicon cassette system (Biomax 8 membrane, Millipore Corporation) to obtain Met-hGH.

EXAMPLE 20

Activation of Met-hGH

After adding 4 liters of 50 mM Tris/HCl and 8 M guanidine hydrochloride solution (pH 8.5) to 1 kg of cells obtained in Reference 2, the cells were dissolved, whereupon centrifugation (10,000 rpm) was conducted. To approximately 4 liters of supernatant obtained, 44 liters of 50 mM Tris/acetic acid, 5.45 mM cysteine hydrochloride monohydrate, 109 mM arginine, and 4.91 M urea solution (pH 8.0) was added, and the activation was conducted for 3 days at 4° C. The amount of activated Met-hGH obtained was approximately 1.2 times more than that obtained in Example 19. Following the activation, the solution was concentrated and desalted in a Pellicon cassette system (Biomax 8 membrane, Millipore Corporation) while adding 25 liters of 20 mM Tris/acetic acid and 2.5 M urea solution (pH 8.0) until the electric conductivity was no greater than 5 mS/cm. Desalting was conducted again while adding 35 liters of 20 mM Tris/acetic acid solution (pH 8.0), whereupon centrifugation (10,000 rpm) was performed to obtain supernatant. Subsequently, the supernatant was applied to a DEAE-Toyopearl 650 column (30 cm$\phi$×60 cm, Tosoh Corporation) equilibrated with 20 mM Tris/acetic acid solution (pH 8.0) for adsorption, followed by a thorough wash using 20 mM Tris/acetic acid solution (pH 8.0) and 20 mM Tris/acetic acid, and 25 mM sodium chloride solution (pH 8.0), followed by elution with 20 mM Tris/acetic acid and 55 mM sodium chloride solution (pH 8.0), to obtain 50 liters of eluate as Met-hGH fractions. This eluate was concentrated and desalted in a Pellicon cassette system (Biomax 8 membrane, Millipore corporation) to obtain Met-hGH.

EXAMPLE 21

Activation of Met-hGH

After adding 5 milliliters of 50 mM Tris/acetic acid and 8 M guanidine hydrochloride solution (pH 8.5) to 1.25 g of cells obtained in Reference 2, the cells were dissolved, whereupon centrifugation (10,000 rpm) was conducted. To approximately 5 milliliters of supernatant obtained, 55 milliliters of 50 mM Tris/acetic acid, 5.45 mM N-acetyl-L-cysteine, 109 mM arginine, and 4.91 M urea solution (pH 8.0) was added, and activation was conducted for 3 days at 4° C. The resulting activation efficiency observed was equivalent to that observed in Example 20, wherein cysteine hydrochloride monohydrate was added.

EXAMPLE 22

Activation of Met-hGH 5 milliliters of 50 mM Tris/acetic acid and 8 M guanidine hydrochloride solution (pH 8.5) was added to 1.25 g of cells obtained in Reference 2 to dissolve the cells, and centrifugation (10,000 rpm) was conducted. To approximately 5 milliliters of supernatant obtained, 55 milliliters of 50 mM Tris/acetic acid, 5.45 mM cysteamine hydrochloride, 109 mM arginine, and 4.91 M urea solution (pH 8.0) was added, and activation was conducted for 3 days at 4° C. The resulting activation efficiency observed was equivalent to that observed in Example 20, where cysteine hydrochloride monohydrate was added.

EXAMPLE 23

Human neurotrophin-3 possessing N-terminal methionine residue (Met-NT-3) was manufactured according to the method described in Reference 3 of Unexamined Kokai Application Heisei 10-72489 (EP-A-812856).

50 mg of human neurotrophin-3 possessing methionine on the N-terminal (Met-NT-3) was dissolved into 8 ml of 3 M urea solution, whereupon a mixture comprising 0.4 ml of 0.2 M cupric sulfate, 0.5 g of glyoxylic acid, and 1 ml of pyridine was added to bring the total to 10 ml, whereupon it was allowed to react for 1 hour at 25° C. After termination of the reaction, the reaction solution was made to flow through a Sephadex G-25 column 125 mm ID×66 mmL) equilibrated with 2.5 M urea+10 mM phosphate buffer solution (pH 6.0), the solution used for equilibration developed at a flow rate of 4 ml/minute, and NT-3 fractions possessing diketone of the methionine residue were pooled. Subsequently, an equal volume of 2 M acetic acid, 4 M sodium formate, and 3 M urea solution was added to these fractions, followed by the addition of 3,4-diaminobenzoic acid to bring the concentration to 40 mM, to be allowed to react for 5 days at 25° C. After the reaction, the reaction solution was made to flow through a Sephadex G-25 column (46 mm ID×600 mmL) equilibrated with 2.5 M urea+10 mM phosphate buffer solution (pH 6.0), the buffer solution used for equilibration developed at a flow rate of 10 ml/minute, and human neurotrophin-3 without N-terminal methionine residue (NT-3) fractions were pooled. After adjusting the pH of the pooled NT-3 fractions to 5.0, said fractions were applied to a CM-5PW (21.5 mm ID×150 mmL, Tosoh Corporation) equilibrated with 50 mM phosphate buffer solution+0.2 M NaCl+2.5 M urea (pH 5.0) for adsorption, followed by elution at a flow rate of 6 ml/minute on a step gradient of 0 to 100% B (B=50 mM phosphate buffer solution+0.2 M NaCl +2.5 M urea, pH 8.0) for 60 minutes, to pool NT-3 fractions. Further, the NT-3 fractions were made to adsorb to a C4P-50 (21.5 mm ID×300 mmL, Showa Denko K.K.) equilibrated with 0.1% TFA, followed by elution at a flow rate of 5 ml/minute on a step gradient of 20 to mn 60% B (B=80% acetonitrile/0.1% TFA) for 40 minutes. After pooling, the NT-3 fractions were lyophilized, to yield approximately 5 mg of NT-3 in lyophilized powder form.

EXAMPLE 24

Characterization of NT-3 a) N-terminal Amino Acid Sequence Analysis

The N-terminal amino acid sequence was determined using a gas phase protein sequencer (Applied Biosystems Model 477A). The amino acid sequence thus obtained matched the NT-3 N-terminal amino acid sequence that was deduced from the cDNA base sequence (Table 12).

TABLE 12

| Residue No. | PTH[1]) Amino acid detected (pmol) | Amino acid deduced from NT-3 base sequence |
| --- | --- | --- |
| 1 | Tyr (410) | Tyr |
| 2 | Ala (521) | Ala |
| 3 | Glu (155) | Glu |
| 4 | His (213) | His |
| 5 | Lys (587) | Lys |
| 6 | Ser (91) | Ser |
| 7 | His (161) | His |
| 8 | Arg (318) | Arg |
| 9 | Gly (214) | Gly |
| 10 | Glu (108) | Glu |
| 11 | Tyr (104) | Tyr |
| 12 | Ser (50) | Ser |
| 13 | Val (208) | Val |
| 14 | N.D. | Cys |
| 15 | Asp (99) | Asp |
| 16 | Ser (41) | Ser |
| 17 | Glu (24) | Glu |
| 18 | Ser (27) | Ser |
| 19 | Leu (63) | Leu |
| 20 | Trp (26) | Trp |

Analysis was conducted using 1 nmol.
N.D.: Not detected.
*) Phenylthiohydantoin b) Amino Acid Composition Analysis The amino acid composition was determined using an amino acid analyzer (Beckman System 6300E). The amino acid composition thus obtained matched the amino acid composition deduced from the NT-3 cDNA base sequence (Table 13).

TABLE 13

| Amino acid | Number of residues per mole | Value deduced from NT-3 base sequence |
| --- | --- | --- |
| Asx | 11.0 | 11 |
| Thr*) | 8.7 | 9 |
| Ser*) | 10.4 | 12 |
| Glx | 11.0 | 11 |
| Pro | 1.7 | 2 |
| Gly | 8.0 | 8 |
| Ala | 4.8 | 5 |
| Cys | N.D. | 6 |
| Val | 8.7 | 9 |
| Met | 0 | 0 |
| Ile | 6.7 | 7 |
| Leu | 5.0 | 5 |
| Tyr | 5.1 | 5 |
| Phe | 1.2 | 1 |
| His | 4.3 | 4 |

TABLE 13-continued

| Amino acid | Number of residues per mole | Value deduced from NT-3 base sequence |
| --- | --- | --- |
| Lys | 9.7 | 10 |
| Arg | 9.6 | 10 |
| Trp | 3.8 | 4 |

Acid hydrolysis (mean value of 24-hour and 48-hour hydrolysis, at 110° C., with 6N hydrochloric acid - 4% thioglycolic acid).
N.D.: Not detected.
*)Value extrapolated at 0 hours.
Analysis was performed using ca 20 μg.

d) C-terminal Amino Acid Analysis

The C-terminal amino acid was determined using an amino acid analyzer (Beckman System 6300E). The amino acid thus obtained matched the C-terminal amino acid deduced from the cDNA base sequence (Table 14).

TABLE 14

| NT-3 | C-terminal amino acid | Recovery rate (%) |
| --- | --- | --- |
| | Thr | 42.0 |

Phase hydrazinolysis (at 100° C. for 3.5 hours)
Analysis was performed using 15 nmol.

e) Biological Activity of NT-3

The biological activity of the NT-3 obtained in Example 23 was measured using DRG (dorsal root ganglia, taken from the embryos of fertilized chicken eggs upon embryogenesis following 8 to 10 days of incubation at 37.5° C.) bioassay, whereupon it was confirmed that said NT-3 possessed a degree of activity equivalent to that of NT-3 obtained from CHO cells.

EXAMPLE 25

After adding 6 M urea solution to 14.75 ml of the Met-hGH solution obtained in Example 2 to bring the total to 60 ml, a mixture comprising 1.2 ml of 0.5 M cupric sulfate, 3.75 g of glyoxylic acid, and 7.5 ml of pyridine was added to bring the total to 75 ml, whereupon it was allowed to react for 1 hour at 25° C. After termination of the reaction, the reaction solution was made to flow through a Sephadex G-25 column (4.6 cm ID×60 cmL) equilibrated with 4 M urea+20 mM Tris buffer solution (pH 8.0), the buffer solution used for equilibration developed at a flow rate of 10 ml/minute, to pool hGH fractions possessing diketone of the methionine residue. Subsequently, an equal volume of 2 M acetic acid, 4 M sodium formate, and 4 M urea solution was added to these fractions, followed by the addition of 3,4-diaminobenzoic acid to bring the concentration to 40 mM, to be allowed to react for 4 days at 30° C. After termination of the reaction, the reaction solution was made to flow through a Sephadex G-25 column (11.3 cm ID×80 cmL) equilibrated with 4 M urea+20 mM Tris buffer solution (pH 8.0), the buffer solution used for equilibration developed at a flow rate of 30 ml/minute, and hGH fractions without N-terminal methionine residue were pooled. The pooled hGH fractions were applied to a DEAE-5PW (5.5 cm ID×20 cmL, Tosoh Corporation) equilibrated with 50 mM Tris buffer solution+ 2.5 M urea (pH 8.0) for adsorption, followed by elution at a flow rate of 15 ml/minute on a step gradient of 0 to 100% B (B=50 mM MES+2.5 M urea, pH 4.0) for 60 minutes, to obtain approximately 60 mg of hGH.

EXAMPLE 26

Preparation of Human Apelin-36 Structural Gene

The 6 types of DNA fragments shown in FIG. 4 (#1 and #5: Greiner Japan Co. Ltd.; #2 and #6: Kikotec Co.; #3 and

Figure 5:
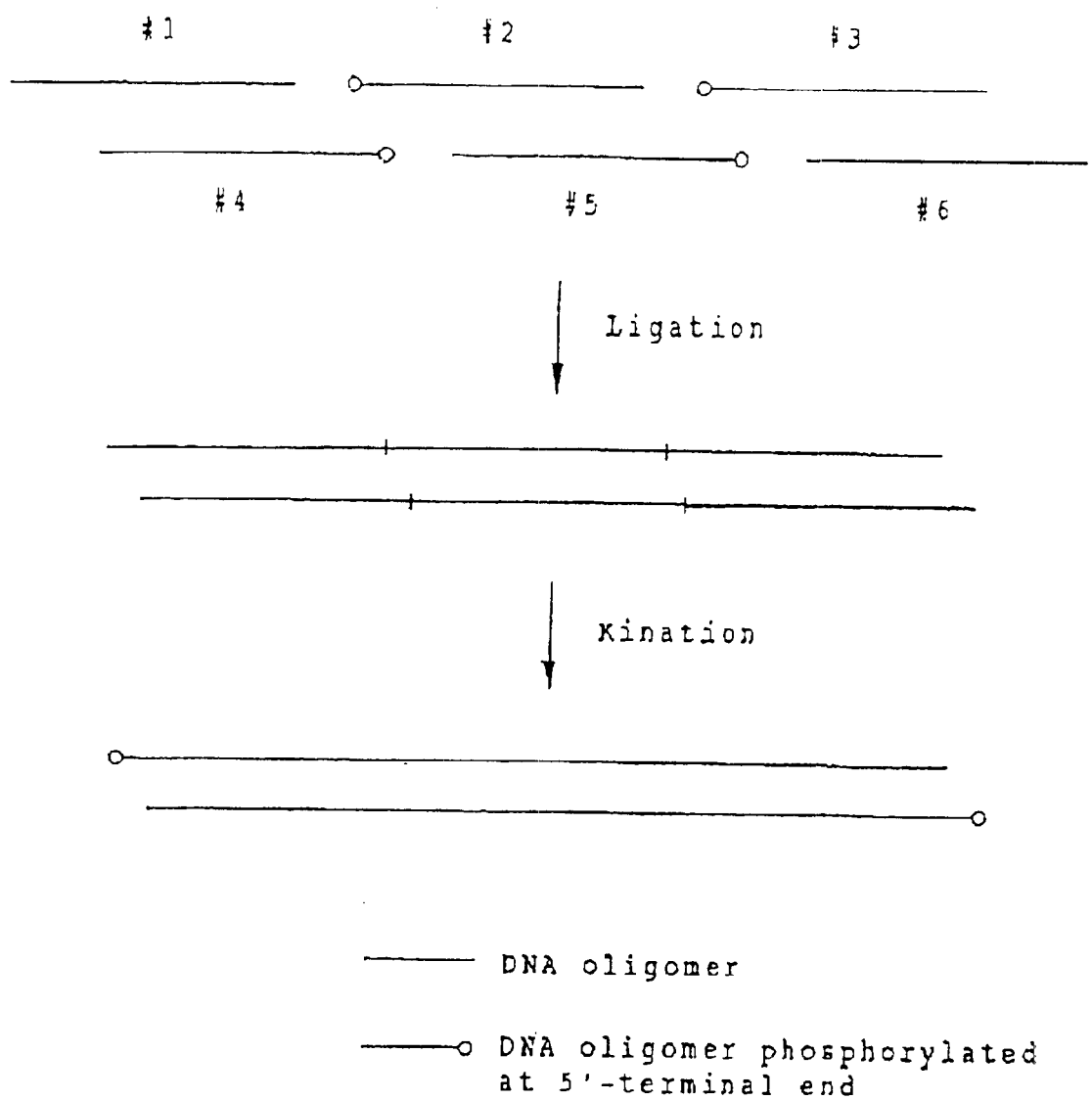
FIG. 5 is an illustration of the schematic diagram for manufacturing the double chain human apelin-36 obtained in Example 26.

4: Amersham Pharmacia Biotech) were used to prepare the apelin-36 structural gene (FIG. 5).

a) Phosphorylation of DNA Oligomer

With the exclusion of oligomers #1 and #6, 1 μg each of the remaining 4 types of oligomers destined to become 5' terminals was allowed to react for 1 hour at 37° C. in 100 μL of phosphorylation reaction solution [50 mM Tris/HCl (pH 7.6), 10 mM $MgCl_2$, 1 mM spermidine, 10 mM dithiothreitol, 0.1 mg/mL bovine serum albumin, 1 mM ATP, 10 units of T4 polynucleotide kinase (Nippon Gene)], to phosphorylate the 5' terminals. After phenol extraction, the aqueous phase was recovered, 2 volumes of ethanol was added, followed by cooling to −70° C., then by centrifuge to precipitate the DNA.

b) Ligation of DNA Fragments

The phosphorylated DNA fragments obtained in a) above were combined with 1 μg each of #1 and #2 to make a total of 120 μL. After maintaining this mixture at 80° C. for 10 minutes, said mixture was cooled slowly to room temperature for annealing the fragments. TaKaRa DNA Ligation Kit ver. 2 (Takara Shuzo) was used to perform the ligation reaction. After adding 30 μL of Solution II to 30 μL of the annealing solution and mixing well, 60 μL of Solution I was added, and allowed to react for 1 hour at 37° C. to perform the ligation. After phenol extraction, the aqueous phase was recovered, 2 volumes of ethanol was added, followed by cooling to −70° C., then by centrifuge to precipitate the DNA.

c) Phosphorylation of the 5' Terminal

The precipitate was dissolved in 10 μL of TE buffer solution (10 mM Tris/HCl (pH 8.0) and 1 mM EDTA), then allowed to react for 1 hour at 37° C. in 100 μL of phosphorylation reaction solution [50 mM Tris/HCl (pH 7.6), 10 mM $MgCl_2$, 1 mM spermidine, 10 mM dithiothreitol, 0.1 mg/mL bovine serum albumin, 1 mM ATP, 10 units of T4 polynucleotide kinase (Nippon Gene)], to phosphorylate the 5' terminals. After phenol extraction, the aqueous phase was recovered, 2 volumes of ethanol was added, followed by cooling to −0 70° C., then by centrifuge to precipitate the DNA, which was dissolved into 20 μL of TE buffer solution.

EXAMPLE 27

Preparation of Human Apelin-36 Expression Plasmid

Figure 6:
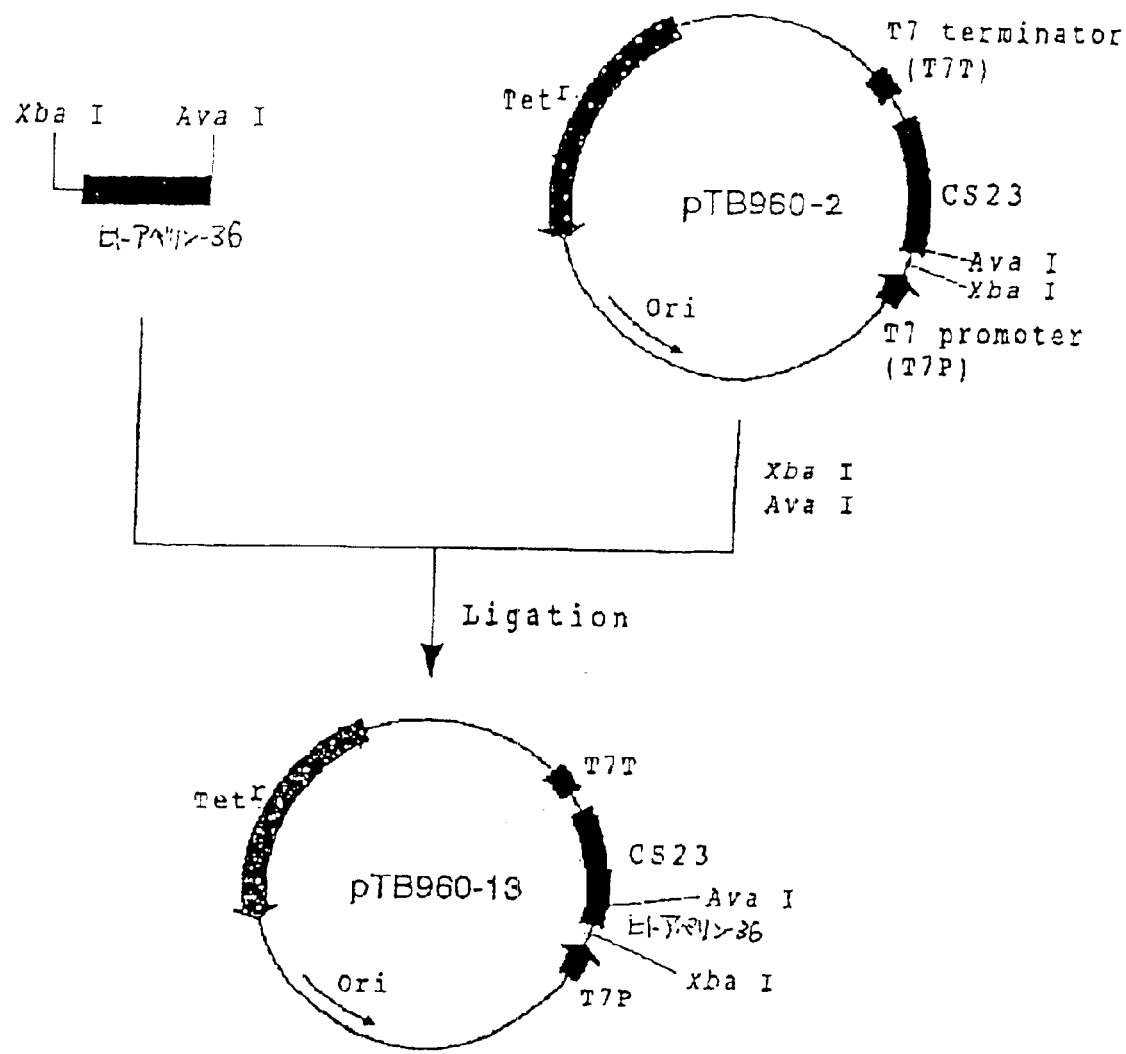
FIG. 6 is an illustration of the structural diagram of plasmid pTB 960-13 obtained in Example 27.

PTB960-2 (EP-A-499990: Koyama et al, Journal of Biotechnology, 32, p. 273) was digested with XbaI and AvaI, followed by 1% agarose electrophoresis, to extract approximately 4.4 Kbp of DNA fragments using QIAquick Gel Extraction Kit (QIAGEN), which were dissolved into 25 μL of TE buffer solution. These XbaI and AvaI fragments of pTB960-2 and the human apelin-36 structural gene prepared using the aforementioned method were subjected to ligation reaction using TaKaRa DNA Ligation Kit ver. 2 (Takara Shuzo). Namely, 1 μl of the pTB96D-2 XbaI and AvaI fragment solution was mixed with 4 μL of human apelin-36 structural gene solution, followed by the addition of 5 μL of Solution I, to be allowed to react for 30 minutes at 16° C. to perform the ligation. 10 μL of the ligation solution was used to transform *E. coli* JM109 competent cells (Toyobo Co. Ltd.), which were then plated on LB agar medium containing 10 μg/mL tetracycline and cultured for 1 day at 37° C., whereupon the tetracycline-resistant colonies generated were selected. These transformants were cultured on LB medium overnight, whereupon QIAprep 8 Miniprep Kit (QIAGEN) was used to prepare plasmid pTB960-13. The base sequence for this human apelin-36 structural gene fragment was verified using an Applied Biosystems Model 377 DNA Sequencer. Plasmid pTB960-13 was used to transform *E. coli* BL21(DE3) strain (Novagen, Inc.), which was then plated on LB agar medium containing 10 μg/mL tetracycline, and cultured for 1 day at 37° C., to obtain human apelin-36-CS23 fusion protein expression strain BL21(DE3)/pTB960-13 (FIG. 6). This transformant *E. coli* BL21(DE3)/pTB960-13 was deposited with the National Institute of Bioscience and Human-Technology of the Agency of Industrial Science and Technology of the Ministry of International Trade and Industry on Dec. 2, 1998, under accession number FERM BP-6590, and with the Institution for Fermentation, Osaka (IFO) on Nov. 11, 1998, under accession number IFO 16220.

EXAMPLE 28

The transformed cells obtained in Example 27 were cultured with shaking for 8 hours at 37° C. within a 2-liter flask containing 1 L of LB medium (1% peptone, 0.5% yeast extract, 0.5% sodium chloride) containing 5.0 mg/L tetracycline. The culture obtained was transferred to a 50 L fermenter containing 19 liters of fermentation medium (1.68% dibasic sodium phosphate, 0.3% monobasic potassium phosphate, 0.1% ammonium chloride, 0.05% sodium chloride, 0.05% magnesium sulfate, 0.02% antifoaming agent, 0.00025% ferrous sulfate, 0.00025% thiamin hydrochloride, 1.5% glucose, 1.5% casamino acid), to start aeration/agitation at 30° C. When the turbidity of the culture solution was approximately 500 Klett units, isopropyl-β-D-thiogalactopyranoside was added so that the final concentration was 12 mg/L, followed by another 4 hours of cultivation. After termination of cultivation, the culture solution was subjected to centrifugation to obtain approximately 660 g of wet cells, which were then frozen for storage at −80° C.

EXAMPLE 29

Acquisition of Human Apelin-36

1,500 ml of 10 mM EDTA+1 mM (p-amidophenyl)-methanesulfonyl fluoride hydrochloride (pH 6.0) solution was added to 550 g of the cells obtained in Example 28, followed by sonication (Branson Sonifier Model 450), followed by centrifugation (10,000 rpm, 60 min.). The supernatant was pooled, while the precipitate was subjected once again to the same procedure. The pooled supernatant was adjusted the pH to 6.0, then made to flow through an AF-Heparin Toyopearl 650M column (30 mm ID×500 mmL, Tosoh Corporation) equilibrated with 50 mM phosphate buffer solution (pH 6.0) for adsorption, followed by washing, then by elution on a step gradient of 0 to 100% B (B=50 mM phosphate buffer solution+2 M NaCl, pH 6.0), to obtain 530 ml of human apelin-36-CS23 fusion protein fractions.

This eluate was concentrated in a Pellicon Mini cassette (Millipore Corporation) while adding 0.1 M acetic acid, to obtain 0.1 M acetic acid solution of human apelin-36-CS23 fusion protein. After adding urea to this solution so that the final concentration was 6 M, 35 mg of 1-cyano-4-dimethylaminopyridinium (DMAP-CN) was added, and allowed to react for 15 minutes at room temperature. After termination of the reaction, the reaction solution was made to flow through a Sephadex G-25 column (46 mm ID×600 mmL, Pharmacia) equilibrated with 10% acetic acid, the 10% acetic acid used for equilibration developed at a flow rate of 6 ml/min, and S-cyanylated human apelin-36-CS23 fusion protein fractions were obtained. This eluate was concentrated and desalted in a Pellicon Mini cassette (Millipore Corporation), to obtain the desalted solution of human apelin-36-CS23 fusion protein. After adding urea to this desalted solution so that the final concentration was 6 M, 1 N of caustic soda was added to bring the concentration to 0.06 N, and allowed to react for 15 minutes at 0° C. After termination of the reaction, the pH was adjusted to 6.0 with acetic acid, to obtain human apelin-36. This reaction solution was made to flow through an SP-5PW (21.5 mm ID×150 mmL, Tosoh Corporation) equilibrated with 50 mM phosphate buffer solution (pH 6.5) containing 3 M urea, for adsorption, followed by washing, then by elution on a step gradient of 0 to 40% B (B=50 mM phosphate buffer solution+1 M NaCl+3 M urea, pH 6.5), to obtain human apelin-36 fractions. These human apelin-36 fractions were made to flow through a C4P-50 (21.5 mm ID×300 mmL, Showa Denko K.K.) equilibrated with 0.1% trifluoroacetic acid (TFA) for adsorption, followed by washing, then by elution on a step gradient of 15 to 30% B (B: 80% acetonitrile/0.1% TFA), whereupon the human apelin-36 fractions were pooled, then lyophilized, to obtain human apelin-36 lyophilized powder.

a) Amino Acid Composition Analysis

The amino acid composition was determined using an amino acid analyzer (Hitachi L-8500A Amino Acid Analyzer).

The amino acid composition thus obtained matched the amino acid composition deduced from the base sequence of the DNA of human apelin-36 possessing N-terminal methionine (Table 15).

TABLE 15

Amino acid composition analysis

| Amino acid | Number of residues per mole | Value deduced from human apelin-36 base sequence |
|---|---|---|
| Asx | 1.0 | 1 |
| Thr[1] | 0 | 0 |
| Ser[1] | 1.9 | 2 |
| Glx | 3.0 | 3 |
| Pro | 5.7 | 6 |
| Gly | 5.7 | 6 |
| Ala | 0 | 0 |
| Cys[2] | N.D. | 0 |
| Val | 1.0 | 1 |
| Met | 2.0 | 1 |
| Ile | 0 | 0 |
| Leu | 2.0 | 2 |
| Tyr | 0 | 0 |
| Phe | 1.9 | 2 |
| His | 1.0 | 1 |
| Lys | 1.8 | 2 |
| Arg | 7.3 | 8 |
| Trp | 0.9 | 1 |

Acid hydrolysis (24-hour and 48-hour hydrolysis, at 110° C., with 6N hydrochloric acid - 4% thioglycolic acid).
[1]Value extrapolated at 0 hours.
[2]Not detected.

b) N-terminal Amino Acid Sequence Analysis

The N-terminal amino acid sequence was determined using a gas phase protein sequencer (Applied Biosystems Model 477A). Other than the human apelin-36 amino acid sequence thus obtained possessing a methionine residue on the N-terminal, said sequence matched the N-terminal amino acid sequence that was deduced from the DNA base sequence (Table 16).

TABLE 16

N-terminal amino acid sequence

| Residue No. | PTH[1] Amino acid detected (pmol) | Amino acid deduced from human apelin-36 base sequence |
|---|---|---|
| 1 | Met (526) | |
| 2 | Leu (648) | Leu |
| 3 | Val (513) | Val |
| 4 | Gln (437) | Gln |
| 5 | Pro (463) | Pro |
| 6 | Arg (216) | Arg |
| 7 | Gly (232) | Gly |
| 8 | Ser (129) | Ser |
| 9 | Arg (129) | Arg |
| 10 | Asn (142) | Asn |
| 11 | Gly (185) | Gly |
| 12 | Pro (219) | Pro |
| 13 | Gly (202) | Gly |
| 14 | Pro (188) | Pro |
| 15 | Trp (88) | Trp |
| 16 | Gln (116) | Gln |
| 17 | Gly (120) | Gly |
| 18 | Gly (72) | Gly |
| 19 | Arg (56) | Arg |
| 20 | Arg (40) | Arg |

Analysis was conducted using 1 nmol.
[1]Phenylthiohydantoin c) C-terminal Amino Acid Analysis The C-terminal amino acid was analyzed using an amino acid analyzer (Hitachi L-8500A Amino Acid Analyzer) (Table 17).

TABLE 17

C-terminal amino acid analysis

| Human apelin-36 | C-terminal amino acid | Recovery rate (%) |
|---|---|---|
| | Phe | 38.6 |

Phase hydrazinolysis (at 100° C. for 6 hours)

The above analysis identified the human apelin-36 obtained in Example 29 as belonging to a molecular species that possesses methionine residue on the N-terminal (Met-apelin-36 (human)).

EXAMPLE 30

Measurement of Biological Activity

The Met-apelin-36 (human) obtained in Example 29 was used to measure activity according to the method (Cytosensor) described in Example 6 of Patent Application Heisei 10-271645, whereupon said Met-apelin-36 (human) was verified to possess activity equivalent to that of synthetic human apelin-36.

EXAMPLE 31

Removal of N-terminal Methionine Residue

After dissolving 4 mg of the Met-apelin-36 (human) obtained in Example 29 into 0.8 ml of 3 M urea solution. a mixture comprising 0.05 ml of 80 mM cupric sulfate, 30 0.046 g of glyoxylic acid, and 0.1 ml of pyridine was added and allowed to react for 1 hour at 25° C. After termination of the reaction, the reaction solution was made to flow through a Sephadex G-25 column (10 mm ID×250 mmL) equilibrated with 2.5 M urea+10 mM phosphate buffer solution (pH 5.5), the solution used for equilibration developed at a flow rate of 0.5 ml/minute, and human apelin-36 fractions possessing diketone of the methionine residue were pooled. Subsequently, an equal volume of 2 M sodium formate, 4 M acetic acid, and 3 M urea solution was added to these fractions, followed by the addition of 3,4-diaminobenzoic acid so that the concentration was 40 mM, to be allowed to react for 3 days at 30° C. After termination of the reaction, the reaction solution was made to flow through a Sephadex G-25 column (25 mm ID×600 mmL) equilibrated with 50 mM phosphate buffer solution (pH 6.0), the buffer solution used for equilibration developed at a flow rate of 4 ml/minute, and human apelin-36 fractions without N-terminal methionine residue were pooled. The pooled human apelin-36 fractions were adjusted the pH to 6.0, then adsorbed to a CM-5PW (7.5 mm ID×75 mmL, Tosoh Corporation) equilibrated with 50 mM phosphate buffer solution+0.1 M NaCl+2.5 M urea (pH 5.0), followed by elution on a step gradient of 0 to 100% B (B=50 mM borate buffer solution+0.1 M NaCl+2.5 M urea, pH 9.0) for 40 minutes at a flow rate of 0.8 ml/minute, whereupon human apelin-36 fractions were pooled. The human apelin-36 was then adsorbed to a C4P-50 (10 mm ID×250 mmL, Showa Denko K.K.) equilibrated with 0.1% TFA, followed by elution on a step gradient of 15 to 30% B (B=80% acetonitrile/0.1% TFA) for 40 minutes at a flow rate of 2 ml/minute. Upon pooling human apelin-36 fractions, said fractions were lyophilized, to yield human apelin-36.

a) Amino Acid Composition Analysis

The amino acid composition was determined using an amino acid analyzer (Hitachi L-8500A Amino Acid Analyzer).

The amino acid composition thus obtained matched the amino acid composition deduced from the base sequence of the DNA of hA10L (Table 18).

TABLE 18

Amino acid composition analysis

| Amino acid | Number of residues per mole | Value deduced from the human apelin-36 base sequence |
| --- | --- | --- |
| Asx | 1.0 | 1 |
| Thr[1] | 0 | 0 |
| Ser[1] | 1.9 | 2 |
| Glx | 2.9 | 3 |
| Pro | 6.3 | 6 |
| Gly | 5.9 | 6 |
| Ala | 0 | 0 |
| Cys[2] | N.D. | 0 |
| Val | 1.0 | 1 |
| Met | 1.0 | 1 |
| Ile | 0 | 0 |
| Leu | 2.0 | 2 |
| Tyr | 0 | 0 |
| Phe | 1.9 | 2 |
| His | 1.0 | 1 |
| Lys | 1.9 | 2 |
| Arg | 7.6 | 8 |
| Trp | 0.9 | 1 |

Acid hydrolysis (24-hour and 48-hour hydrolysis, at 110° C., with 6N hydrochloric acid - 4% thioglycolic acid).
[1]Value extrapolated at 0 hours.
[2]Not detected.

b) N-terminal Amino Acid Sequence Analysis

The terminal amino acid sequence was determined using a gas phase protein sequencer (Applied Biosystems Model 477A). The amino acid sequence thus obtained matched the N-terminal amino acid sequence that was deduced from the base sequence of the DNA of the human apelin-36 obtained (Table 19).

TABLE 19

N-terminal amino acid sequence

| Residue No. | PTH[1] Amino acid detected (pmol) | Amino acid deduced from human apelin-36 base sequence |
| --- | --- | --- |
| 1 | Leu (475) | Leu |
| 2 | Val (845) | Val |
| 3 | Gln (365) | Gln |
| 4 | Pro (563) | Pro |
| 5 | Arg (425) | Arg |
| 6 | Gly (424) | Gly |
| 7 | Ser 138) | Ser |
| 8 | Arg (423) | Arg |
| 9 | Asn (245) | Asn |
| 10 | Gly (290) | Gly |
| 11 | Pro (197) | Pro |
| 12 | Gly (234) | Gly |
| 13 | Pro (197) | Pro |
| 14 | Trp (101) | Trp |
| 15 | Gln (76) | Gln |
| 16 | Gly (84) | Gly |
| 17 | Gly (130) | Gly |
| 18 | Arg (79) | Arg |
| 19 | Arg (116) | Arg |
| 20 | Lys (43) | Lys |

Analysis was conducted using 1 nmol.
[1]Phenylthiohydantoin c) C-terminal Amino Acid Analysis The C-terminal amino acid was analyzed using an amino acid analyzer (Hitachi L-8500A Amino Acid Analyzer) (Table 20).

TABLE 20

C-terminal amino acid analysis

| Human apelin-36 | C-terminal amino acid | Recovery rate (%) |
| --- | --- | --- |
|  | Phe | 86.6 |

Phase hydrazinolysis (at 100° C. for 6 hours)

EXAMPLE 32

Measurement of Biological Activity

The human apelin-36 obtained in Example 31 was used to measure activity according to the method (cytosensor) described in Example 6 of Patent Application Heisei 10-271646, whereupon said human apelin-36 was verified to possess activity equivalent to that of synthetic human apelin-36.

INDUSTRIAL APPLICABILITY

The present invention makes possible the selective, specific and efficient removal of methionine residue from peptides, proteins, or the salts thereof which possess optionally oxidized N-terminal methionine residue, and makes possible the efficient production of peptides, proteins, or the salts thereof which do not possess optionally oxidized U-terminal methionine residue. Additionally, according to the methods of the present invention, the chemical removal of the N-terminal methionine residue is possible under mild conditions regardless of the type of peptide or protein, thereby making possible the industrially advantageous manufacture of peptides or proteins possessing wild-type amino acid sequences using, as raw material, genetically engineered peptides, proteins, or the salts thereof which possess methionine residue.

What is claimed is:

1. A method for removing 2-oxo-4-(methylsulfanyl) butanoic acid from the N-terminus of a peptide comprising the step of reacting a peptide bearing an N-terminal 2-oxo-4-(methylsulfanyl)butanoic acid with 3,4-diaminobenzoic acid in the presence of a mixture selected from the group consisting of acetic acid and sodium formate, formic acid and sodium formate, and formic acid and sodium acetate, for a time and under conditions effective to remove the 2-oxo-4-(methylsulfanyl)butanoic acid from the N-terminus of the peptide.

2. The method described in claim 1 wherein the peptide which possesses the N-terminal 2-oxo-4-(methylsulfanyl) butanoic acid is a peptide or a salt thereof which is obtained by having a peptide or a salt thereof which possesses an N-terminal 2-amino-4-(methylsulfanyl)butanoic acid react with an alpha-keto carboxylic acid.

3. The method described in claim 2 wherein the peptide which possesses the N-terminal 2-oxo-4-(methylsulfanyl) butanoic acid is a peptide which has been manufactured by genetic engineering technology.

4. The method described in claim 1 wherein the peptide is selected from the group consisting of (i) a growth hormone, (ii) beta-cellulin, (iii) interleukin-2, (iv) neurotrophin-3, and (v) apelin.

5. The method described in claim 1 wherein the peptide is a growth hormone.

6. The method described in claim 1, wherein the acetic acid and sodium formate, formic acid and sodium formate, or formic acid and sodium acetate is used as a buffer solution of approximately 0.1 to 8 mol/L, with a pH of approximately 2 to 9.

7. A method for removing 2-oxo-4-(methylsulfanyl) butanoic acid from the N-terminus of a peptide comprising the step of reacting a peptide bearing an N-terminal 2-oxo-4-(methylsulfanyl)butanoic acid with 3,4-diaminobenzoic acid in the presence of acetic acid and sodium formate, for a time and under conditions effective to remove the 2-oxo-4-(methylsulfanyl)butanoic acid from the N-terminus of the peptide.

8. A method for the manufacture of a peptide which does not possess an N-terminal 2-amino-4-(methylsulfanyl) butanoic acid, which comprises reacting a peptide possessing 2-oxo-4-(methylsulfanyl)butanoic acid with 3,4-diaminobenzoic acid in the presence of a mixture selected from the group consisting of acetic acid and sodium formate, formic acid and sodium formate, and formic acid and sodium acetate, for a time and under conditions effective to remove the 2-oxo-4-(methylsulfanyl)butanoic acid from the N-terminus of the peptide.

9. The method of manufacture described in claim 8 wherein the peptide which possesses an N-terminal 2-oxo-4-(methylsulfanyl)butanoic acid is a peptide or a salt thereof obtained by having a peptide or a salt thereof which possesses an N-terminal 2-amino-4-(methylsulfanyl)butanoic acid react with an alpha-keto carboxylic acid.

10. The method of manufacture described in claim 8, wherein the acetic acid and sodium formate, formic acid and sodium formate, or formic acid and sodium acetate is used as a buffer solution of approximately 0.1 to 8 mol/L, with a pH of approximately 2 to 9.

11. A method for manufacturing a peptide or a salt thereof which does not possess an N-terminal 2-amino4-(methylsulfanyl)butanoic acid, which comprises reacting a peptide or salt thereof which possesses an N-terminal 2-oxo-4-(methylsulfanyl)butanoic acid with 3,4-diaminobenzoic acid in the presence of acetic acid and sodium formate, for a time and under conditions effective to remove the 2-oxo-4-(methylsulfanyl)butanoic acid from the N-terminus of the peptide.

12. A method for manufacturing human growth hormone or a salt thereof which does not possess an N-terminal 2-amino4-(methylsulfanyl)butanoic acid, which comprises reacting a genetically engineered peptide or salt thereof which possesses an N-terminal 2-amino4-(methylsulfanyl) butanoic acid with glyoxylic acid or a salt thereof in the presence of cupric sulfate and pyridine to obtain a reaction product, then reacting the reaction product with 3,4-diaminobenzoic acid in the presence of a mixture selected from the group consisting of acetic acid and sodium formate, formic acid and sodium formate, or formic acid and sodium acetate, for a time and under conditions effective to remove the 2-amino-4-(methylsulfanyl)butanoic acid from the N-terminus of the peptide.

\* \* \* \* \*